US010881642B2

(12) United States Patent
Lee et al.

(10) Patent No.: US 10,881,642 B2
(45) Date of Patent: Jan. 5, 2021

(54) AUTOPHAGY ENHANCER AND USE THEREOF

(71) Applicants: Industry-Academic Cooperation Foundation, Yonsei University, Seoul (KR); Gwangju Institute of Science and Technology, Gwangju (KR)

(72) Inventors: Myung-Shik Lee, Seoul (KR); Hyejin Lim, Suwon-si (KR); Young Eui Jeon, Anyang-si (KR); Jin Hee Ahn, Gwangju (KR); H. S. Pagire, Gwangju (KR)

(73) Assignees: Industry-Academic Cooperation Foundation, Yonsei University, Seoul (KR); Gwangju Institute of Science and Technology, Gwangju (KR)

( * ) Notice: Subject to any disclaimer, the term of this patent is extended or adjusted under 35 U.S.C. 154(b) by 0 days.

(21) Appl. No.: 16/316,913

(22) PCT Filed: Jun. 29, 2017

(86) PCT No.: PCT/KR2017/006894
§ 371 (c)(1),
(2) Date: Jan. 10, 2019

(87) PCT Pub. No.: WO2018/012769
PCT Pub. Date: Jan. 18, 2018

(65) Prior Publication Data
US 2019/0336483 A1 Nov. 7, 2019

(30) Foreign Application Priority Data

Jul. 12, 2016 (KR) .................. 10-2016-0087862
Jun. 28, 2017 (KR) .................. 10-2017-0081671

(51) Int. Cl.
*A61K 31/421* (2006.01)
*A61P 3/04* (2006.01)
(Continued)

(52) U.S. Cl.
CPC ............ *A61K 31/421* (2013.01); *A61P 3/04* (2018.01); *A61P 3/06* (2018.01); *G01N 33/5041* (2013.01);
(Continued)

(58) Field of Classification Search
CPC ............ A61K 31/421; A61P 3/04; A61P 3/06
See application file for complete search history.

(56) References Cited

U.S. PATENT DOCUMENTS

2014/0134661 A1   5/2014 White et al.
2016/0136123 A1   5/2016 Deretic et al.

FOREIGN PATENT DOCUMENTS

WO   2008/061248 A2   5/2008

OTHER PUBLICATIONS

Hale et al., (2013) Autophagy, 9:7, 951-972 (Year: 2013).*
(Continued)

*Primary Examiner* — San Ming R Hui
(74) *Attorney, Agent, or Firm* — Vorys, Sater, Seymour & Pease LLP; Mih Suhn Koh

(57) ABSTRACT

Provided are a compound of chemical formula 1 or 2 and a use thereof. The compound can be advantageously used in the prevention or treatment of metabolic diseases including type 2 diabetes, insulin resistance, or obesity, on the basis of a mechanism of autophagy activation through the promotion of lysosome production.

7 Claims, 35 Drawing Sheets

Specification includes a Sequence Listing.

(51) Int. Cl.
*A61P 3/06* (2006.01)
*G01N 33/50* (2006.01)
(52) U.S. Cl.
CPC ..... *G01N 2500/02* (2013.01); *G01N 2500/10* (2013.01)

(56) References Cited

OTHER PUBLICATIONS

Kim et al., "Amyloidogenic peptide oligomer accumulation in autophagy-deficient BETA cells induces diabetes", J Clin Invest., vol. 124, No. 8, pp. 3311-3324, (2014).
Klionsky et al., "Autophagy as a Regulated Pathway of Cellular Degradation", Science, vol. 290, pp. 1717-1721, (2000).
Mizushima et al., "Autophagy: Renovation of Cells and Tissues", Cell, vol. 147, pp. 728-741, (2011).
Shoji-Kawata et al., "Identification of a candidate therapeutic autophagy-inducing peptide", Nature, vol. 494, pp. 201-209, (2013).

* cited by examiner

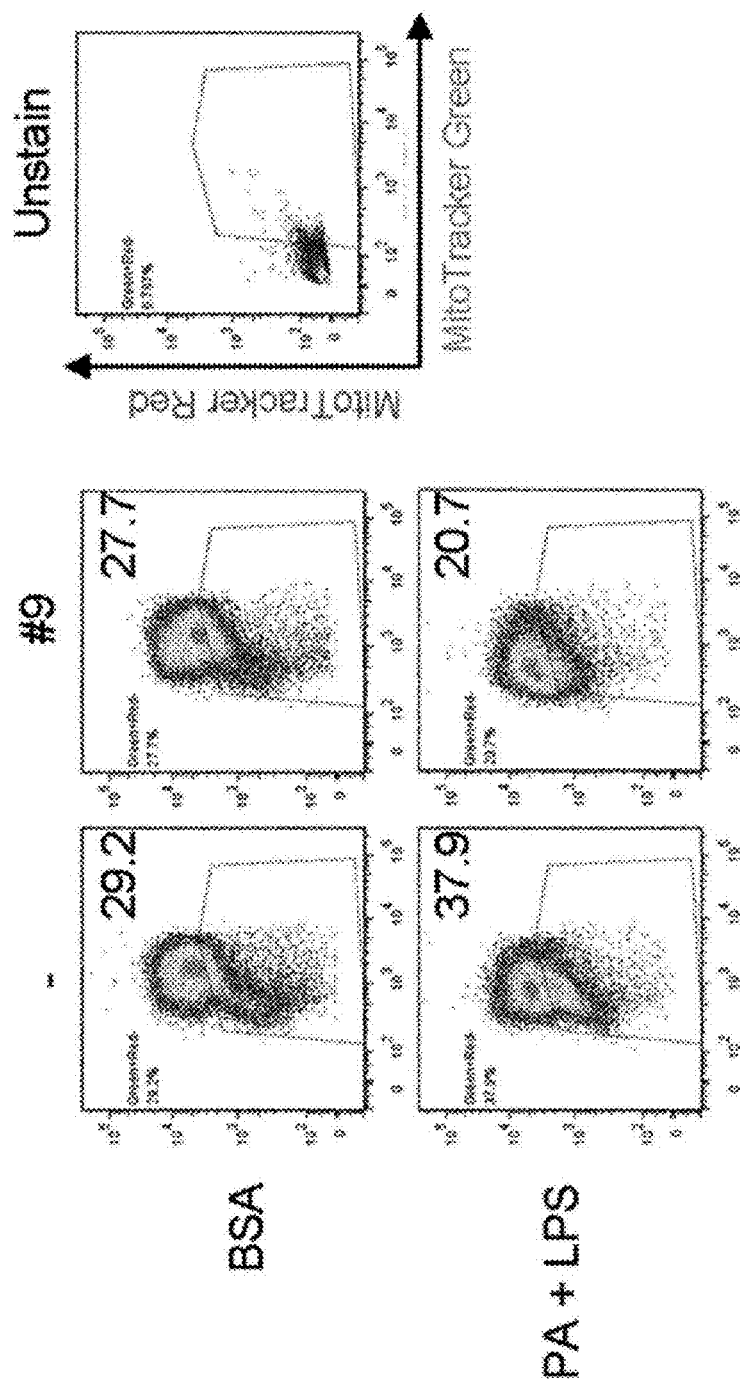

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: TFEB-Forward Primer

<400> SEQUENCE: 1
ccagaagcga gagctcacag at                                              22

<210> SEQ ID NO 2
<211> LENGTH: 22
<212> TYPE: DNA
<213> ORGANISM: Artificial Sequence
<220> FEATURE:
<223> OTHER INFORMATION: TFEB-Reverse Primer

<400> SEQUENCE: 2
tgtgattgtc tttcttctgc cg                                              22

<210> SEQ ID NO 3
<211> LENGTH: 22
<212> TYPE: DNA
<213> ORGANISM: Artificial Sequence
<220> FEATURE:
<223> OTHER INFORMATION: MCOLN1-Forward Primer

<400> SEQUENCE: 3
ttgctctctg ccagcggtac ta                                              22

<210> SEQ ID NO 4
<211> LENGTH: 22
<212> TYPE: DNA
<213> ORGANISM: Artificial Sequence
<220> FEATURE:
<223> OTHER INFORMATION: MCOLN1-Reverse Primer

<400> SEQUENCE: 4
gcagtcagta accaccatcg ga                                              22
```

```
<210> SEQ ID NO 5
<211> LENGTH: 20
<212> TYPE: DNA
<213> ORGANISM: Artificial Sequence
<220> FEATURE:
<223> OTHER INFORMATION: UVRAG-Forward Primer

<400> SEQUENCE: 5
ctgtttggat gggctgaaat                                                    20

<210> SEQ ID NO 6
<211> LENGTH: 20
<212> TYPE: DNA
<213> ORGANISM: Artificial Sequence
<220> FEATURE:
<223> OTHER INFORMATION: UVRAG-Reverse Primer
<220> FEATURE:
<221> NAME/KEY: misc_feature
<222> LOCATION: (1)
<223> OTHER INFORMATION: Y is C or T

<400> SEQUENCE: 6
ygcgaacaca gttctgatcc                                                    20

<210> SEQ ID NO 7
<211> LENGTH: 21
<212> TYPE: DNA
<213> ORGANISM: Artificial Sequence
<220> FEATURE:
<223> OTHER INFORMATION: CLCN7-Forward Primer

<400> SEQUENCE: 7
tgatctccac gttcaccctg a                                                  21

<210> SEQ ID NO 8
<211> LENGTH: 21
<212> TYPE: DNA
<213> ORGANISM: Artificial Sequence
<220> FEATURE:
<223> OTHER INFORMATION: CLCN7-Reverse Primer

<400> SEQUENCE: 8
tctccgagtc aaaccttccg a                                                  21

<210> SEQ ID NO 9
<211> LENGTH: 21
<212> TYPE: DNA
<213> ORGANISM: Artificial Sequence
<220> FEATURE:
<223> OTHER INFORMATION: LAMP1-Forward Primer

<400> SEQUENCE: 9
acgttacagc gtccagctca t                                                  21

<210> SEQ ID NO 10
<211> LENGTH: 19
<212> TYPE: DNA
<213> ORGANISM: Artificial Sequence
<220> FEATURE:
<223> OTHER INFORMATION: LAMP1-Reverse Primer

<400> SEQUENCE: 10
tctttggagc tcgcattgg                                                     19
```

```
<210> SEQ ID NO 11
<211> LENGTH: 21
<212> TYPE: DNA
<213> ORGANISM: Artificial Sequence
<220> FEATURE:
<223> OTHER INFORMATION: CTSA-Forward Primer

<400> SEQUENCE: 11
caggctttgg tcttctctcc a                                              21

<210> SEQ ID NO 12
<211> LENGTH: 20
<212> TYPE: DNA
<213> ORGANISM: Artificial Sequence
<220> FEATURE:
<223> OTHER INFORMATION: CTSA-Reverse Primer

<400> SEQUENCE: 12
tcacgcattc caggtctttg                                                20

<210> SEQ ID NO 13
<211> LENGTH: 21
<212> TYPE: DNA
<213> ORGANISM: Artificial Sequence
<220> FEATURE:
<223> OTHER INFORMATION: CTSD-Forward Primer

<400> SEQUENCE: 13
aactgctgga catcgcttgc t                                              21

<210> SEQ ID NO 14
<211> LENGTH: 22
<212> TYPE: DNA
<213> ORGANISM: Artificial Sequence
<220> FEATURE:
<223> OTHER INFORMATION: CTSD-Reverse Primer

<400> SEQUENCE: 14
cattcttcac gtaggtgctg ga                                             22

<210> SEQ ID NO 15
<211> LENGTH: 22
<212> TYPE: DNA
<213> ORGANISM: Artificial Sequence
<220> FEATURE:
<223> OTHER INFORMATION: CTSF-Forward Primer

<400> SEQUENCE: 15
acagaggagg agttccgcac ta                                             22

<210> SEQ ID NO 16
<211> LENGTH: 21
<212> TYPE: DNA
<213> ORGANISM: Artificial Sequence
<220> FEATURE:
<223> OTHER INFORMATION: CTSF-Reverse Primer

<400> SEQUENCE: 16
gcttgcttca tcttgttgcc a                                              21
```

```
<210> SEQ ID NO 17
<211> LENGTH: 22
<212> TYPE: DNA
<213> ORGANISM: Artificial Sequence
<220> FEATURE:
<223> OTHER INFORMATION: ATP6V0E1-Forward Primer

<400> SEQUENCE: 17
cattgtgatg agcgtgttct gg                                              22

<210> SEQ ID NO 18
<211> LENGTH: 22
<212> TYPE: DNA
<213> ORGANISM: Artificial Sequence
<220> FEATURE:
<223> OTHER INFORMATION: ATP6V0E1-Reverse Primer

<400> SEQUENCE: 18
aactccccgg ttaggaccct ta                                              22

<210> SEQ ID NO 19
<211> LENGTH: 21
<212> TYPE: DNA
<213> ORGANISM: Artificial Sequence
<220> FEATURE:
<223> OTHER INFORMATION: ATP6V1H-Forward Primer

<400> SEQUENCE: 19
ggaagtgtca gatgatcccc a                                               21

<210> SEQ ID NO 20
<211> LENGTH: 20
<212> TYPE: DNA
<213> ORGANISM: Artificial Sequence
<220> FEATURE:
<223> OTHER INFORMATION: ATP6V1H-Reverse Primer

<400> SEQUENCE: 20
ccgtttgcct cgtggataat                                                 20

<210> SEQ ID NO 21
<211> LENGTH: 20
<212> TYPE: DNA
<213> ORGANISM: Artificial Sequence
<220> FEATURE:
<223> OTHER INFORMATION: GAPDH-Forward Primer

<400> SEQUENCE: 21
tgcaccacca actgcttagc                                                 20

<210> SEQ ID NO 22
<211> LENGTH: 21
<212> TYPE: DNA
<213> ORGANISM: Artificial Sequence
<220> FEATURE:
<223> OTHER INFORMATION: GAPDH-Reverse Primer

<400> SEQUENCE: 22
ggcatggact gtggtcatga g                                               21
```

AUTOPHAGY ENHANCER AND USE THEREOF

CROSS-REFERENCE TO RELATED APPLICATIONS

The present application is a national phase application of International Patent Application PCT/KR2017/006894, filed Jun. 29, 2017, which claims the benefit of Korean Patent Application No. 2016-0087862 and 2017-0081671, filed Jul. 12, 2016 and Jun. 28, 2017, respectively, in the Korean Intellectual Property Office, the disclosure of which are incorporated herein.

SEQUENCE LISTING

The Sequence Listing submitted in text format (.txt) filed on Jun. 14, 2019, named "SequenceListing.txt", created on Jun. 14, 2019 (4.77 KB), is incorporated herein by reference.

BACKGROUND OF THE INVENTION

Field of the Invention

The present invention relates to agents for regulating autophagy and its use for treating disease associated with autophagy.

Description of the Related Art

Autophagy is a lysosomal-dependent cellular process involving degradation and modulation of cell's own components and includes macroautophagy, microautophagy and chaperone-mediated autophagy. Among them, macroautophagy (referred to as autophagy hereinafter) is characterized by the rearrangement of subcellular membranes sequestering cytoplasm and organelles to form a new organelle-like structure (macro autophagosome). Autophagosomes are fused to lysosomes forming autophagolysosomes where the sequestered materials are degraded by lysosomal enzymes (Klionsky, D J, and Emr, S D (2000) Autophagy as a regulated pathway of cellular degradation. Science 290, 1717-1721). Physiological roles of autophagy include quality control of organelles or cellular proteins and protection of nutrient balance (Mizushima, N, and Komatsu, M (2011) Autophagy: renovation of cells and tissues. Cell 147, 728-741):

Because autophagy is critically involved in the control of cellular metabolic balance of diverse essential nutrients such as amino acids, lipids and glucose, autophagy is expected to play a crucial role in the maintenance of whole body metabolism in the physiological condition. On the other hand, dysregulated autophagy may participate in the development of metabolic disorders such as diabetes and metabolic syndrome in the pathological condition. Particularly in diabetes, autophagy could be an important element in the various aspects of the disease because insulin and its downstream factor mTOR (mechanistic target of rapamycin) are well-known inhibitors of autophagy (Sarbassov, D D et al. (2005) Growing roles for the mTOR pathway. Curr Opin Cell Biol 17, 596-603), while glucagon, a counterregulatory hormone of insulin, is an activator of autophagy. These lead to the notion that autophagy may play an important role in various aspects of diabetes. Furthermore, integrity of organelles such as endoplasmic reticulum (ER) or mitochondria that are essential for pancreatic cell function and insulin sensitivity relies on autophagy (Mizushima, 2011 ibid).

Since autophagy plays a key role in both mobilization of lipids and proteins and recycling of damaged organelles, a deficiency in autophagy activity causes intercellular accumulation of excess fat, aggregated proteins, and dysfunctional organelles which cause metabolic disturbance or diabetes.

Thus, in vivo role of autophagy in diabetes and metabolic syndrome has been extensively studied using various genetic models with altered autophagy in specific tissues or in a systemic manner (Kim, J, et al. (2014) Amyloidogenic peptide oligomer accumulation in autophagy-deficient b-cells leads to diabetes. J Clin Invest 125, 3311-3324). Such mice show diverse metabolic features depending on the location and severity of autophagy deficiency (Coupe, B et al. (2012) Loss of autophagy in pro-opiomelanocortin neurons perturbs axon growth and causes metabolic dysregulation. Cell Metab 15, 1-9). Despite complicated and conflicting metabolic effects of altered autophagy in various tissues in the regulation of energy metabolism, systemically enhanced autophagic activity may have beneficial effects on body metabolism in vivo, particularly in association with metabolic stress or obesity (Kim et al, 2014 ibid). Furthermore, a recent paper showed that mitophagic activity, an important part of autophagic activity, is significantly reduced in vivo in metabolically stressed condition due to high-fat feeding or aging both of which are important players in the development of diabetes, suggesting the possibility that enhancement of autophagic activity may reverse underlying causes of metabolic syndrome or diabetes (Sun, N et al. (2015) Measuring In Vivo Mitophagy. Mol Cell 60, 685-696).

Since autophagy is involved in a broad spectrum of biological processes and a variety of diseases, search for autophagy modulators has been conducted in an attempt to develop novel classes of compounds with therapeutic effects against neurodegeneration, infectious diseases, cancer or aging. For example, numerous autophagy enhancers including natural compounds, compounds with known function, or novel compounds have been developed (Eisenberg, T et al. (2009) Induction of autophagy by spermidine promotes longevity, Nature Cell Biol 11, 1305-1314; Shoji-Kawata, S et al. (2013) Identification of a candidate therapeutic autophagy-inducing peptide. Nature 494, 201-206).

US Patent Publication No. 2014-0134661 discloses a screening method for autophagy enhancer in which p62 is used as a marker and materials affecting the protein are selected as a potential enhancer.

However, previously developed enhancers are not studied for its involvement in metabolic disorders and thus their effects on the metabolic disease, diabetes and the like remain unidentified. Rather they may have an adverse effect on treating metabolic disorder since their interactions with mTOR are not clearly identified. The suppression of mTOR can lead to the enhancement of autophagy; however, it may aggravate the diabetes because it may lead to the reduction of pancreatic islet cells thus lowering the insulin secretion. Thus there is a need to develop autophagy enhancer that can enhance the autophagy activity indecently of mTOR.

SUMMARY OF THE INVENTION

The present disclosure is to provide autophagy regulator through regulating the biogenesis of lysosome and compositions for treating or preventing type 2 diabetes, insulin resistance and obesity.

In one aspect of the present disclosure, there is provided a pharmaceutical composition for treating or preventing metabolic disorder comprising a compound of formula 1 or 2 below or pharmaceutically acceptable salts thereof:

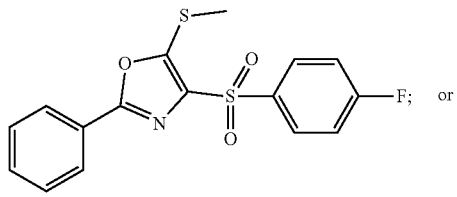

[Formula 1]

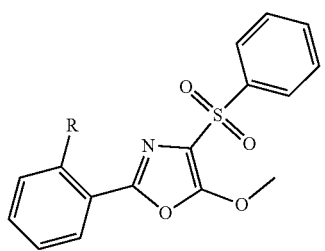

[Formula 2]

wherein R is F, Cl or Br in Formula 2.

The present compounds or the present composition can be advantageously used for treating or preventing metabolic disorder or metabolic syndrome including one or more symptoms of an insulin resistance, Type 2 diabetes, hyperlipidemia, obesity or inflammation.

The present compound have a function of enhancing, improving, promoting or activating autophagy, thus can be effectively used for treating various disease that may be developed from a depletion of autophagy. Further the present compound does not inhibit the function of mTOR, and thus can be effectively used for treating or preventing metabolic disorder or metabolic syndrome including one or more symptoms of an insulin resistance, Type 2 diabetes, hyperlipidemia, obesity or inflammation.

The present compound can enhance the autophagic activity through promoting calcineurin activity, TFEB (Transcription Factor EB) activity, and lysosome biogenesis without inhibiting mTOR.

Thus, in other aspect, there is provided a method or kit to increasing the activity of autophagy through promoting the lysosome biogenesis using the present compound of formula 1 or 2.

In still other aspect, there is provided a kit to remove fat or lipid of cells via promoting the lysosome biogenesis without inhibiting mTOR comprising the present compound of formula 1 or 2.

In still other aspect, there is provided a method of enhancing the autophagic activity in vitro or in vivo by contacting the cells with the present compounds of formula 1 or 2, wherein the contact causes the translocation of TFEB to a nucleus without inhibiting mTOR.

In still other aspect, there is provided a method of removing fat or lipid from cells in vivo or in vitro by contacting the cells with the present compounds of formula 1 or 2, wherein the contact causes the enhancement of autophagic activity which leads to the removal of the fat or lipids from cells.

In still other aspect, there is provided a method of screening a therapeutic agent for treating or preventing metabolic disease based on the mechanism identified in the present disclosure, the method comprises: providing eukaryotic cells, wherein the cells expresses TFEB, Calcineurin and have autophagic activity; subjecting the cells to a metabolic stress; treating the cells with testing compounds; measuring the activity of calcineurin, TFEB (Transcription Factor EB) and autophagy in the cells; and selecting the compounds as a potential therapeutic agent for treating or preventing metabolic disorder when the activity of calcineurin, TFEB and autophagy in the cells is increased compared to that of control cells which is not treated with testing compounds in the measurement step.

In still other aspect, there is provided a compound of formula 2, a derivative of formula 1, as below.

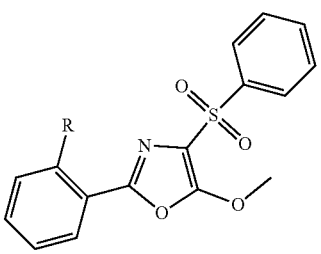

[Formula 2]

wherein R is F, Cl or Br.

As provided is a use for compound of formula 1 or 2 for treating obesity.

As provided is a use for compound of formula 1 or 2 for treating metabolic disorder.

The present compound of formula 1 (MSL) and formula 2 (MSL-7) can enhance the autophagic activity by improving the function of lysosome. Thus the present compounds can be advantageously used for treating or preventing various diseases due to dysfunction of autophagy, particularly metabolic disease including such as obesity, type 2 diabetes and insulin resistance. Particularly, the present compounds function independently of mTOR mechanism, thus obviating the possible side effect of the conventional agents that are reducing the pancreatic islet cells by suppressing mTOR leading to lowering the amount of insulin secreted. Thus the present compounds can be effectively used as therapeutics for treating type 2 diabetes.

BRIEF DESCRIPTION OF THE DRAWINGS

FIG. 1 indicates the results of a screening assay to select novel autophagy enhancers based on luciferase analysis in accordance of the present disclosure. FIG. 1C, FIGS. 1D and 1E is the results in which the cells were treated with 2ndary screened compounds followed by lysis and immunoblotting using the antibody as indicated.

FIG. 2 indicates the results of the Hela Cells treated with Compound of formula I (hereinafter referred to as MSL) showing the increase of the autophagic flux in the cells treated.

FIG. 3 indicates that MSL treatment controls the nuclear translocation of TFEB by calcineurin activation.

FIG. 4 indicates the present compound MSL increases the clearance of the lipid droplet.

FIG. 5 is the results indicating the present compound MSL reduces the activation of inflammasome and enhances the function of mitochondria. FIG. 5B and FIG. 5C is the result of the experiment in which primary peritoneal macrophages were treated with the same condition as described in FIG. 5A, and then the cells were treated with MitoSOX (FIG. 5B) to measure the ROS of mitochondria, or the cells were treated with MitoTracker Red and Mitotracker Green to measure the potential of mitochondria by FACS analysis, in which the numbers indicate the percent of cells at the designated gate. The results indicate that the present compound MSL can effectively improve/treat metabolic disease by improving the inflammation which increases in metabolic disease and improve the mitochondrial function.

FIG. 6 is the results indicating that the present compound MSL improves the metabolic parameters in ob/ob mice.

FIG. 7 indicates that the present MSL compound enhances the autophagic flux in vivo.

FIG. 8 indicates that MSL of the present disclosure improves the inflammation associated with metabolism and the fatty liver.

FIG. 10A is the result of immunoblot using the antibodies indicated using Hela cells treated with MSL or MSL-7. FIG. 10B is the result of measuring the viability of Hela cells treated with vehicle control or various concentration of MSL-7 (50-100 μM) for 48 hrs. FIG. 10C is the result of DAPI stained nuclei of TFEB-GFP HeLa cells which were treated with vehicle control or MSL-7 for 4 hrs. The graph indicates the percentage of TFEB translocated into the nuclei. Error bars, S.D. *, P<0.05; , P<0.01; *, P<0.001. The results indicate that MSL-7, a derivative of MSL compound also enhances the autophagy.

FIG. 12 indicates the improvement of the metabolic profile of HFD-feed mice by MSL-7.

FIG. 13 indicates that the function of β-cell and metabolic profile of mice with diabetes of human type by MSL-7.

DETAILED DESCRIPTION OF THE EMBODIMENTS

Figure 1A:
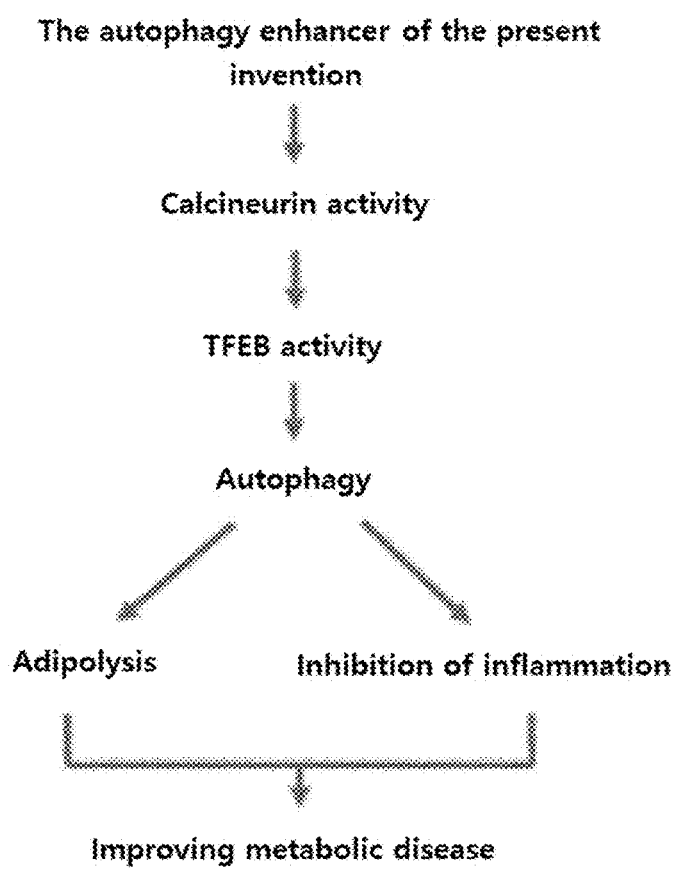
FIG. 1A indicates a schematic diagram of the mechanism identified in the present disclosure.

The present invention based on the discovery of the small molecules capable of enhancing the autophagy by up-regulating the lysosome biogenesis independently of mTOR. The present small molecules were discovered by screening a compound library using autophagic flux analysis based on luciferase assay.

In one aspect, the present disclosure relates to a pharmaceutical composition for treating or preventing metabolic disease, comprising compound of formula 1 (MSL) or formula 2 (MSL-7) as indicated below or pharmaceutically acceptable salts thereof:

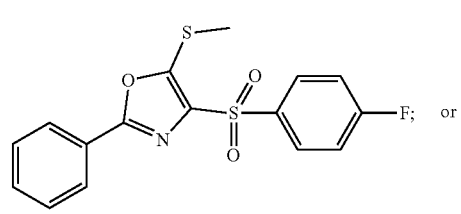

[Formula 1]

or

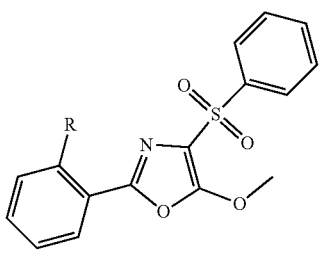

[Formula 2]

wherein, in formula 2, R is F, Cl, or Br.

In other aspect, the present disclosure relates to a compound of formula 2 (MSL-7) as indicated below, having enhancing the autophagic activity.

The compound of formula 2 of the present disclosure can be synthesized by a method of following reaction scheme 1.

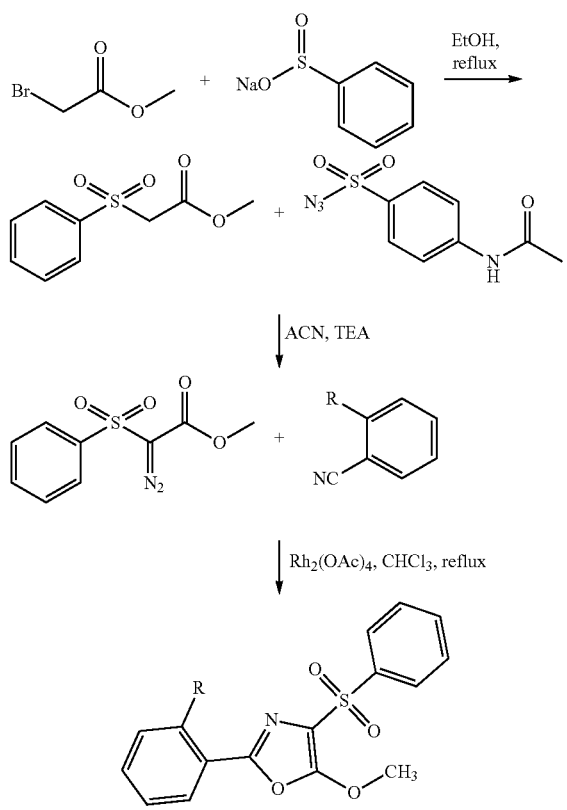

[Reaction scheme 1]

wherein, R is F, Cl or Br.

In the step 1 of the reaction scheme 1, benzenesulfonylacetate methyl ester can be synthesized using bromoacetate methylester. The reaction can be performed using organic solvent such as methanol, ethanol or isopropanol for from 2 to 30 hrs at RT to the boiling point of the solvent.

In the step 2 of the reaction scheme 1, azaid compound is used to synthesize diazocompound (diazo transfer). In the reaction, 4-acetoamidobenzenesulfonyl azaid, tosyl azaid and the like may be used. The reaction can be performed using organic solvent such as acetonifril, or dichloromethane and the like in the presence of bases such as TEA.

In the step 3 of the reaction scheme 1, oxazole ring can be formed. The reaction can be carried out in the presence of a catalyst Rhodium (II). As a catalyst Rhodium (II), $Rh_2(OAc)_2$, or $Rh_2(CF_3CONH)_2$ and the like may be used.

The reaction scheme described above represents just one of many methods which can be used for synthesizing the present compounds and thus different reaction conditions may be employed according to the methods which may be practiced by an ordinary person in the pertinent art, or other methods may be also employed to synthesize the present compounds.

The compounds according to the present disclosure activate or enhance the autophagy and thus can be advantageously used for preventing or treating various diseases which may be benefit from autophagy enhancement.

In the present disclosure, autophagy or autophagocytosis refers to a catabolism to remove various cellular components comprising denatured proteins or unnecessary proteins in the cells using the action of lysosome. The regulation of autophagy is necessary for normal synthesis, degradation and recycling of the cellular components. During the autophagy process, autophagosomes are formed, which are then fused with lysosome and the cellular components are degraded or recycled. Autophagy includes macroautophagy, microautophagy and chaperone-mediated autophagy, which are included in the scope of the present disclosure. Particularly, macroautophagy is included in the present disclosure.

The term modulation in the present disclosure refers to activation of a biological function, stimulation or up-regulation, or decrease or down-regulation, or both. In one embodiment, modulation refers to the activation of a biological function. Further, the modulation includes a modulation in in vitro condition, in vivo condition, or ex-vivo condition.

Because autophagy is closely related to the metabolic regulation of various nutrients such as amino acids, lipids, and glucose, it also plays an important role in the maintenance of a whole body metabolism. Thus, dysregulation of autophagy may lead to the development of metabolic disease such as insulin resistance syndrome including obesity, diabetes and insulin resistance. Major two factors of type 2 diabetes are insulin resistance and dysfunction of beta cells. However, the etiology of type 2 diabetes is not known at the molecular and cellular level. INK activation, NF-kB activation, and low grade tissue inflammation due to accumulation of excess lipids, chemokine and cytokines are important molecular mechanism (Arkan, M C et al. (2005) IKK-beta links inflammation to obesity-induced insulin resistance. Nat Med 11, 191-198; Vandanmagsar, B et al. (2011) The NLRP3 inflammasome instigate obesity-induced inflammation and insulin resistance. Nat Med 15, 179-188). At the level of organelles, dysfunction of ER and mitochondria and stress is also considered major factors for causing diabetes (Ozcan, U et al. (2004) Endoplasmic reticulum stress links obesity, insulin action, and type 2 Diabetes. Science 306, 457-461; Petersen, K F et al. (2003) Mitochondrial dysfunction in the elderly: possible role in insulin resistance. Science 300, 1140-1142), which may affect up-stream or down-stream level of the molecular mechanism described above. The autophagy activity is reduced in the condition where excess lipid is present or in the aging process, thus the lack of autophagy may lead to the dysfunction of ER and mitochondria. Therefore the lack of autophagy can by a basic cause for diabetes and metabolic syndrome related to obesity and aging.

Therefore, the compound of the present disclosure having the activity for enhancing autophagy can be advantageously used for treating or preventing metabolic disease or metabolic syndrome, insulin resistance, type 2 diabetes, hyperlipidemia, or obesity, or inflammation due to obesity and the like.

In the present disclosure, metabolic disease or metabolic syndrome refers to a disease or condition where a subject suffers from multiple disease state or condition such as type 2 diabetes, hyperlipidemia, obesity and/or inflammation due to a fundamental abnormality of metabolism (Pershadsingh HA, Dual Peroxisome Proliferator-Activated Receptor-alpha/gamma Agonists: In the Treatment of Type 2 Diabetes Mellitus and the Metabolic Syndrome. Treat Endocrinol. 2006; 5(2):89-99).

In the present disclosure, the term obesity refers to a disease or condition where a subject has a fat accumulated in the body at a higher level than the normal level due to energy imbalance. According to WHO, in the Asia-Pacific region, the formula used to diagnose obesity is defined as the body weight of a subject divided by square of the height (in meter unit) of a subject, and the value 25.0 or higher is considered obesity, and the value 23 or higher to less than 25 is defined as overweight (weight at risk). Obesity is classified as endocrine obesity (due to endocrine abnormalities or brain diseases), simple obesity (due to excessive nutrition), proliferative obesity (obesity due to increased adipose cell count), hypertrophic type obesity (obesity due to adipose cell size increase); upper body obesity, lower body obesity, and obesity due to excess visceral fat, obesity due to excess subcutaneous fat, and the like, all of which are included in the scope of the present invention In one embodiment, the obesity is the one related to metabolic disease.

In the present disclosure, the terms "treat," "treatment," and "treating" include alleviating, abating or ameliorating at least one symptom of a disease or condition, and/or reducing severity, progression and/or duration thereof, and/or preventing additional symptoms by the administration of the present composition or compound and includes prophylactic and/or therapeutic measures. A person in the ordinary skill in the art in the related art would be able to determine the level or degree of treating, alleviating, abating or ameliorating in reference to the materials disclosed in medical associations and the like.

In the present disclosure, the terms "prevent" or "preventing" include preventing or delaying the development of at least one symptom of a disease or condition by the administration of the present composition or compound. It will be evident to one of the ordinary skill in the art that the present composition when administered before the development of symptoms associated with the suppression of autophagy can prevent the disease disclosed herein.

Therefore, the present compound for enhancing autophagy may be prepared as a pharmaceutical composition. At least one of the pharmaceutical composition may be administered simultaneously or sequentially, or the composition may be administered in combination with other active components for treating the disease disclosed herein.

The present therapeutic or pharmaceutical composition may be formulated into various proper forms with one or more pharmaceutically acceptable carriers. The term "pharmaceutically acceptable" refers to a composition that is physiologically acceptable and does not normally cause an allergic reaction such as a gastrointestinal disorder, dizziness, or a similar reaction and the like when administered to humans. Examples of pharmaceutically acceptable carriers include, but are not limited to, water, suitable oils, saline, aqueous carriers for parenteral administration such as aqueous glucose and glycols, etc., and may additionally contain stabilizers and preservatives. Suitable stabilizers include antioxidants such as sodium hydrogen sulfite, sodium sulphate or ascorbic acid. Suitable preservatives include benzalkonium chloride, methyl- or propyl-paraben and chlorobutanol. In addition, the composition according to the present invention may be further comprises suspensions, solubilizers, stabilizers, isotonizing agents, preservatives, adsorption inhibitors, surfactants, diluents, excipients, pH adjusters, pain killers, buffers, and antioxidant, and the like depending on the particular formulation and route of administration. Pharmaceutically acceptable carriers and formulations suitable for the present invention, including those exemplified above, are described in detail in the latest edition of Remington Pharmaceutical Sciences.

The present composition may be prepared as a unit dosage form or in a form contained in a container by formulating the composition with pharmaceutically acceptable carriers and/or excipients according to the methods which can be practiced without difficulty by one of ordinary skill in the art. The formulations may be in the form of solutions in oil or aqueous media, suspensions or emulsions, or in the form of powders, granules, tablets or capsules.

The rout of administration of the present composition may be selected without difficulty, and may be administered in various route to humans and animals and the like. For example, the present composition may be formulated in the form of powders, tablets, pills, granules, dragees, hard or soft capsules, liquids, emulsions, suspensions, syrups, elixirs, external preparations, suppositories, sterilized injection solutions and the like, and be used for systematic or local administration, or oral or parenteral administration. In one embodiment particularly parenteral administration may be preferred.

Formulations for parenteral administration include sterile aqueous solutions, non-aqueous solutions, suspensions, emulsions, freeze-dried preparations, and suppositories. Examples of the non-aqueous solvent and suspending agent include propylene glycol, polyethylene glycol, vegetable oil such as olive oil, injectable ester such as ethyl oleate, and the like. Witepsol, macrogol, tween 61, cacao paper, laurin, glycerol, gelatin and the like may be used as a base for suppositories.

The dosage of the pharmaceutical composition of the present invention may vary depending on the patient's body weight, age, sex, health condition, diet, administration time, administration method, excretion rate and severity of disease. Effective doses are typically about 1 ng to 10 mg/day, particularly about 1 μg to 1 mg/day for an adult (60 kg). It will be apparent to those skilled in the art that dosages described above may be changed, as the dosage can vary depending on various conditions, and thus the dosage does not in anyway limit the scope of the invention.

The present composition may be administered once or several times a day within a desired range, and the administration period is not particularly limited.

The screening methods used herein are based on the method that resolves the conventional LC3-based assays (Rubinsztein, D C et al. Nat Rev Drug Discov 11, 709-730) which do not have a discrimination of the level of autophagy and autophagy flux. The conventional methods only can measure the level of autophagy and cannot measure autophagy activity. Thus, this may result in that the autophagy suppressor can be mistaken for autophagy enhancer. Also the conventional method of measuring the autophagy activity is suitable for individual assays and not suitable for high-throughput assays. The present method is suitable for measuring autophagy activity in high-throughput.

The compounds according to the present invention enhance the autophagy by promoting the generation of lysosomes. Lysosome generation is an essential constituent for autophagy as described above. Particularly, the compounds of the present invention activate autophagy by promoting lysosomal production independently of mTOR inhibition, i.e., by not inhibiting the mTOR mechanism.

In this perspective, the present compounds relates to a kit for regulating or enhancing autophagy by lysosome generation.

The kits according to the present disclosure may be used in various methods in vivo or in vitro that require to enhance autophagy in cells.

In this perspective, there is disclosed a method of activating or enhancing autophagy in vitro, in vivo or ex vivo, comprising a step of contacting a cell with a compound of formula 1 or 2 of the present disclosure, wherein the contact results in the translocation of TFEB to a nucleus without suppressing mTOR.

Further, it was found in the present disclosure that the present compounds suppress the lipid metabolism and inflammasome activity. The compounds according to the present disclosure promotes the generation of lysosomes, and the generated autophagolysosomes then directly interact with lipids in cells and remove the lipids. Thus the present compounds can enhance the metabolic profile related to excess lipids or obesity.

Thus, in this perspective, there is provided a pharmaceutical composition comprising a compound of formula 1 or 2 or their pharmaceutically acceptable salts of the present disclosure for treating or preventing obesity.

Also, in this perspective, there is provided a kit for removing lipids or fats of cells through promoting the generation of lysosome independently of mTOR suppression.

The kits according to the present disclosure may be used for various methods where require a removal of fat or lipids of cells in vivo or in vitro.

In this perspective, there is provided a method of removing fat from cells in vitro, in vivo and ex vivo, the method comprising a step of contacting compound of formula 1 and 2 of the present disclosure with cells, wherein the contact results in the activation of autophagy leading to a removal of lipids of the cells.

Conventionally the association of autophagy with the development of a disease has been studied mainly in cancers, neurological disorders, and inflammatory disease. There are no reports on the role of autophagy in the development of metabolic disease. In the present disclosure, it has been found that metabolic disease can be treated by controlling autophagy which leads to the control of inflammasome and removal of fat from cells, as well as the underlying molecular mechanism was also identified (Refer to FIG. 1A, FIG. 1B).

Therefore, in other aspect, there is provided a screening method for identifying a therapeutic agent for treating or preventing metabolic disease based on the mechanism identified in the present disclosure.

In one embodiment, the present methods comprise steps of providing eukaryotic cells to be employed in the methods; subjecting the cells under metabolic stress; treating the cells with test agents or test compounds before or after the step of subjecting the cells under metabolic stress; and measuring from the cells the autophagy activity, calcineurin, and TFEB.

As a result of the measuring step, when the cells treated with a particular test agent show increase autophagy activity, calcineurin and TFEB compared to the cells that are not treated with the test agents, the particular agent may be selected as a potential therapeutic agent.

The cells which may be employed in the present disclosure include cells of in vitro or cells present in animals used in experiments, i.e., experimental animal models. Because autophagy, as described hereinbefore, is critical for homeostasis of cells and thus required for proper function of all types of cells, various types of cells having autophagy function may be employed for the present invention. Therefor the cells which may be employed for the present methods are not particularly limited as long as the activity of autophagy, TFEB and calcineurin with or without treatment with test substance can be measured from the cells. The cells may include, but are not limited to, for example, HeLa, TFEB-GFP-HeLa, adipose cells, or liver cells including such as SK-HEP1 (hepatoma cell line) and Hepa1c1c7 (hepatoma cell line).

In the present method, a step of subjecting the cells to a metabolic stress before or after treating the cells with test substance is employed.

As used herein the term metabolic stress refers to a series of process of the cells to recognize and response to various stress particularly the one related to a nutrient stress particularly to a stress when particular nutrients are in excess or insufficient, to meet or maintain the bioenergetics needs of the cells. Particularly in the perspective of metabolic disease, it may be interpreted in terms of activating or inactivating autophagy. Therefore, to screen autophagy regulators according to the present methods, there needs proper treatment steps that can activate or inactivate autophagy by the cells.

In one embodiment, the metabolic stress include, but is not limited to, treating cells with proper lipids for example palmitoic acids or oleic acids, or depleting glucose from cells. A person of ordinary skill in the art would be able to select suitable ones to be employed in the present methods in reference to what is described in the present disclosure including Examples.

In the present method, the method of measuring the activity of autophagy, TFEB and calcineurin are known in the art, and one of ordinary skill in the art would be able to select proper methods without difficulty in reference to what is described in the present Examples. Also the level or degree of the activity of autophagy, TFEB and calcineurin in the cells treated may be determined in comparison to the cells not treated without difficulty in reference to what is described in the present disclosure including Examples.

It is expected in the present methods that the test agents or substances which may be employed in the present methods does not suppress mTOR but induce the activity of autophagy, TFEB and calcineurin. These substances may include, but are not limited to, small molecules, high molecular weight molecules, nucleic acids (such as DNA, RNA, PNA and aptamer), proteins, carbohydrates and lipids and the like.

In one embodiment, small molecules are used to identify agents useful for treating and/or preventing metabolic disease. For example small molecules with molecular weight of about less than 1,000 Da such as 400 Da, 600 Da, or 800 Da. If desired, small molecules may form part of a library, the total number of small molecules included therein may vary from dozens to millions. Test substance of a library may be composed of peptides, peptoides, circular or liner oligomeric compounds, template based compounds such as benzodiazepine, hydantoin, biaryls, carbocyclic and polycyclic compounds such as naphthalene, phenothiazine, acridine, steroids and the like, carbohydrate and amino acid derivatives, dihydropyridine, benzhydryl and heterocyclic compounds such as triazine, indole, thiazolidine and the like, but does not limited thereto. The amount of test substances employed may vary depending on the particular experimental conditions or methods and kinds of the test substances employed, which may be determined without difficulty by one of ordinary skill in the related art.

In other aspect of the present disclosure, there is provided a method of treating metabolic disease in a subject in need thereof, the method comprising a step of administering an effective amount of compound of formula 1 or 2, or composition comprising the same and pharmaceutically acceptable carrier.

References may be made to what is described hereinbefore for the compounds and the composition which may be employed in the present methods.

The present compounds or the present composition may be administered to a subject who is need of treatment or prevention of metabolic disease. The subject includes but is not limited to, mammals including particularly primates, more particularly human.

The present compounds or the composition is administered as therapeutically effective amount. The term "therapeutically effective amount" refers to an amount sufficient to treat a disease at a reasonable benefit/risk ratio applicable to medical treatment and may be determined in consideration of the type of disease, severity, the time of administration, the sensitivity to a drug, the activity of a drug, the route of administration and the rate of release, the duration of the treatment, factors including co-administered drugs, and other factors well known in the medical arts. The composition of the present invention may be administered as an individual therapeutic agent or in combination with other therapeutic agents, sequentially or concurrently with conventional therapeutic agepts, and may be administered once or multiple times. It is important to take into account all of the above factors and to administer the amount in which the maximum effect can be obtained with a minimal amount without side effects, which can be determined without difficulty by those skilled in the art.

The present disclosure is further explained in more detail with reference to the following examples. These examples, however, should not be interpreted as limiting the scope of the present invention in any manner.

EXAMPLES

Experimental Example

Materials and Methods

Screening of autophagy enhancer. HEK 293 cells in a 10 cm culture dish were transfected 5 ug of pRLuc(C124A)-LC3 (wt) or pRLuc(C124A)-LC3(G120A) plasmid using 10 ul lipofectamine (Faskas, Identification of novel autophagy regulators by a luciferase-based assay for the kinetics of autophagic flux. Autophagy 5: 1018-1025, 2009), Stable transfectants were selected by culturing in the presence of 400 µg/ml G418, and clones that showed wild/mutant normalized luciferase ratio of <0.7 after treatment of 125 nM Rapamycin for 6 h were isolated for library screening.

Luciferase assay. Firefly and Renilla luciferase assays were conducted using the Dual-Luciferase Reporter Assay System (Promega) according to the manufacturer's recommendation. In brief, cells were lysed in 1× lysis buffer and subjected to a single round of freezing/thawing. Firefly luciferase was determined after mixing 5 µl of lysate with 25 µl of Luciferase Assay Reagent II. Renilla luciferase was then determined after further addition of 20 ul of Stop&Glo Reagent.

Cell culture and media and drugs treatment. HeLa, TFEB-GFP-HeLa, SK-HEP1 (hepatoma cell line) and Hepa1c1c7 (hepatoma cell line) cells were cultured in the following media: (normal) Dulbecco's modified Eagle's medium (DMEM, Sigma-Aldrich) supplemented with 10% FBS and 1% penicillin/streptomycin; (starvation) HBSS media with Ca and Mg supplemented with 10 mM HEPES; Drugs treatment: MSL compound (50-100 µM); Rapamycin (2.5 mg/ml); Torin-1 (1 µM); Bafilomycin (100 nM); Cyclosporin A (10 µM); and FK506 (5 µM). Cells were treated with oleic acid (400 µM) and palmitic acid (400 µM) for 24 h. Where indicated, cells were washed off with HBSS and replaced by DMEM with or without MSL for 16 h. INS-1 cells, a insulinoma cell line of mice were cultured as described previously (Kim et al., 2014 ibid) in the presence or absence of bafilomycin and treated with MSL-7.

Lactate dehydrogenase (LDH) assay. Cytotoxicity was determined by the measurement of LDH release in cell culture media using the LDH kit (Roche), according to the protocol from the manufacturer.

Transfection and plasmids. Cells were transiently transfected with DNA plasmids 3×FLAG-hTFEB (A Ballabio), FYVE-dsRed (Cantley LC), RFP-LC3 or mRFP-GFP-LC3 using lipofectamine 2000 (Invitrogen) according to the protocol from the manufacturer. INS-1 cells were transfected with prepro-mIAPP-HA or prepro-hIAPP-HA using jetPEIDNA according to the manufacturer's protocol.

Imaging and image quantification. Imaging was performed with a ×40 objective on an LSM780 confocal microscope (Zeiss). Image analysis (spot count per cell) was performed using Image J. When indicated, cells were stained for lipid droplets with BODIPY 493/503 (Invitrogen, 20m/ml, 20 min) according to the manufacturer's methods. Formation of acidic vesicular organelles was quantitated by staining the cells with acridine orange (Invitrogen, 5 ug/ml, 10 min).

Antibodies and western blotting. Cells or tissues were solubilized in lysis buffer supplemented with protease and phosphatase inhibitors and protein concentration was measured by the Bradford method. Ten to 30 micrograms were loaded on 4-12% Bis-Tris gel (NUPAGE, Invitrogen) or 8-15% SDS-PAGE, transferred to PVDF membranes and analyzed by western blot using the ECL method (Pierce). The following antibodies were used: LC3 (Novus NB100-2331, 1:1,000), p62 (Progen GP62-C, 1:1,000), b-actin (Santa Cruz sc-47778, 1:5,000), FLAG (Sigma-Aldrich F1804, 1:2,000), 70S6K (Cell Signaling 9202S, 1:1000), p-70S6K (Cell Signaling 9206S, 1:1000), mTOR (Cell Signaling 2983, 1:1000), pmTOR (Cell Signaling 2971S, 1:1000), TFEB (Cell Signaling 4240, 1:1000). Protein levels were quantified by using ImageJ software analysis.

RNA extraction, RT and real-time RT-PCR. Total RNA was extracted from cells or tissues using TRIzol (Invitrogen) and cDNA was synthesized using MMLV-Rtase (Promega) according to the protocol from the manufacturer. Real-time RT-PCR was performed using SYBR green (Takara) in ABI PRISM 7000 (Applied Biosystems). All expression values were normalized to GAPDH mRNA level. Primers used (5' to 3'): TFEB-F (5'-CCAGAAGCGAGAGCTCACAGAT-3') (SEQ ID NO:1), TFEB-R (5'-TGTGAT-TGTCTTTCTTCTGCCG-3') (SEQ ID NO:2), MCOLN1-F (5-TTGCTCTCTGCCAGCGGTACTA-3') (SEQ ID NO:3), MCOLN1-R (5'-GCAGTCAGTAACCACCATCGGA-3')

(SEQ ID NO:4), UVRAG-F (5'-CTGTTTGGATGGGCT-GAAAT-3') (SEQ ID NO:5), UVRAG-R (5'-YGCGAACACAGTTCTGATCC-3') (SEQ ID NO:6), CLCN7-F (5'-TGATCTCCACGTTCACCCTGA-3') (SEQ ID NO:7), CLCN7-R (5'-TCTCCGAGT-CAAACCTTCCGA-3') (SEQ ID NO:8), LAMP1-F (5'-ACGTTACAGCGTCCAGCTCAT-3') (SEQ ID NO:9), LAMP1-R (5'-TCTTTGGAGCTCGCATTGG-3') (SEQ ID NO:10), CTSA-F (5'-CAGGCTTTGGTCTTCTCTCCA-3') (SEQ ID NO:11), CTSA-R (5'-TCACGCAT-TCCAGGTCTTTG-3') (SEQ ID NO:12), CTSD-F (5'-AACTGCTGGACATCGCTTGCT-3') (SEQ ID NO:13), CTSD-R (5'-CATTCTTCACGTAGGTGCTGGA-3') (SEQ ID NO:14), CTSF-F (5'-ACAGAGGAG-GAGTTCCGCACTA-3') (SEQ ID NO:15), CTSF-R (5'-GCTTGCTTCATCTTGTTGCCA-3') (SEQ ID NO:16), ATP6V0E1-F (5'-CATTGTGATGAGCGTGTTCTGG-3') (SEQ ID NO:17), ATP6V0E1-R (5'-AACTCCCCGGT-TAGGACCCTTA-3') (SEQ ID NO:18), ATP6V1H-F (5'-GGAAGTGTCAGATGATCCCCA-3') (SEQ ID NO:19), ATP6V1H-R (5'-CCGTTTGCCTCGTGGATAAT-3') (SEQ ID NO:20), GAPDH-F (5'-TGCACCACCAACTGCT-TAGC-3') (SEQ ID NO:21), and GAPDH-R (5'-GG-CATGGACTGTGGTCATGAG-3') (SEQ ID NO:22).

GCaMP3 Ca2+ Imaging. HeLa cells were grown on 15 mm coverslips and transfected with plasmid encoding the peri-lysosomal-localized ML1-GCaMP3 calcium probes. The fluorescence intensity at 470 nm was monitored using the LSM780 confocal microscope (Zeiss). After 48 h, lysosomal Ca2+ release was measured under a basal Ca2+ solution, which contained 145 mM NaCl, 5 mM KCl, 3 mM MgCl2, 10 mM glucose, 1 mM EGTA, 20 mM HEPES (pH 7.4) with or without MSL. GPN (200 µM, a lysosome-disrupting agent) was used as positive controls to induce Ca2+ release from lysosome. Ionomycin (1 µM) was added at the conclusion of all experiments to induce a maximal response for comparison.

Calcineurin Phosphatase Activity Assay. The phosphatase activity of calcineurin was detected using cellular calcineurin phosphatase activity assay kit (Abcam, ab139464) according to the protocol from the manufacturer.

Histology. Tissue samples were fixed in 10% buffered formalin and embedded in paraffin. Sections (5 µm) were stained with hematoxylin-eosin stain for morphometry, or processed to detect F4/80 positive macrophages aggregated in crown-like structures (CLS) surrounding adipocytes. To detect IAPP oligomer, frozen pancreas section was immune-stained with A11 antibody (Millipore), and then incubated in the presence of Alexa 488-conjugated goat anti-rabbit immunoglobin G and observed with confocal microscopy.

Amyloid Staining. Deparaffinized pancrease section was treated with 70% formic acid for 20 min and then incubated in the presence of 10 mM FSB (Millipore) for 1 hr. DAPI-counter stained section was examined under fluorescent microscope (Nikon). The average fluorescent intensity/area was measured with NIS-Elements AR 3.0 software (Nikon).

IL-1β ELISA assay. Primary peritoneal macrophages were isolated from C57BL/6 mice using 3.85% thioglycollate medium, and treated with PA in the presence or absence of 500 ng/ml LPS. After incubation for 24 h, IL-1β content in culture supernatants was assayed using a mouse ELISA kit (R&D Systems) according to the manufacturer's method.

Mitochondrial changes. To determine mitochondrial potential, peritoneal macrophages were stained with 1 µM each of MitoTracker Green and MitoTracker Red (Invitrogen) at 37° C. for 25 min. Cells were suspended in 1% FBS in PBS for analysis on a FACSVerse (BD Biosciences) using FlowJo software (TreeStar). To measure mitochondrial ROS content, cells were incubated with 5 µM MitoSOX (Invitrogen) at 37° C. for 5 min, and fluorescence activated cell sorting analysis was done as above.

Mouse experiments. Male ob/ob mice (6-8 weeks) were purchased from Jackson. Mice were maintained in a 12-h light/12-h dark cycle and fed a chow diet. Ob/ob mice were treated with vehicle (n=9), MSL, or MSL-7 (n=9) during 8 weeks (intraperitoneally injection; 50 mg/kg/2 days). During the treatment period the treated mice were monitored and weighted. For the experiments using diet-induced obesity models, 8-week-old male C57BL/6 mice were fed HFD for 8 weeks, and then treated with 50 mg/kg MSL or MSL-7 3 times a week for 8 weeks together with HFD feeding. Transgenic mice expressing amyloid generating hIAPP (hIAPP+ mice) (Jackson Laboratory) were maintained as described above (Kim et al., 2014, ibid). 16 week old male hIAPP+ mice were fed HFD to promote the accumulation of oligomer, and at the same time MSL-7 was also administered. All the animal experiments were performed in accordance with the guidance of the public health services for laboratory animal use. Ob/Ob mice were treated with vehicle (n=9) or MSL (n=9) (intraperitoneal injection; 50 mg/kg/2 days) for 8 weeks. The mice was monitored and their body weight was measured during the treatment period. Mice experiments were approved by IACUC Institutional Animal Care and Use Committee, AAALAC-accredited unit of Yonsei University.

Intraperitoneal glucose tolerance (IPGTT) and insulin tolerance tests (ITT). IPGTT was performed by intraperitoneal injection of 1 g/kg glucose after overnight fasting. Blood glucose concentrations were determined using an One Touch glucometer (Lifescan) before (0 min) and 15, 30, 60, 120 and 180 min after glucose injection. ITT was conducted by injecting 0.75 U/kg of regular insulin intraperitoneally to fasted mice and measuring blood glucose levels at 0, 15, 30, 60 and 120 min. Serum insulin concentrations were determined using an ELISA kit (Shibayagi). HOMA-IR was calculated using the following formula: (fasting insulin× fasting glucose)/22.5. Insulinogenic index was calculated as follows: (insulin 15 min-insulin 0 min)/(glucose 15 min-glucose 0 min).

Blood chemistry. Measurement of serum ALT/AST, TG, total cholesterol, ALP, ALB, DBIL, GTT and LDH levels was performed using a Fuji Dri-Chem blood chemistry analyzer according to the manufacturer's instructions. Hamevet950 Blood Analyzer (Drew Scientific) according to the manufacturer's instructions to obtain a hemogram from heparinized blood.

TG measurement. For biochemical measurement of TG content, lipid was extracted from homogenized tissue using chloroform/methanol mixture (2:1). Lipid residue after evaporation was suspended in 1% Triton X-100 in 100% ethanol, and mixed with Free Glycerol Reagent. After incubation at 37° C. for 5 min, A540 was measured for calculation of TG concentrations on a standard curve.

Liver microsomal stability. The reaction mixture consisted of human liver microsomes (BD Gentest) in 100 mM potassium phosphate buffer (pH 7.4) and 10 µM test chemicals. After preincubation at 37° C. for 5 min, the reaction was initiated by adding NADPH regenerating solution (BD Biosciences). Samples (50 µl) were collected at 0 and 30 min. The reaction was terminated by adding 450 µl of ice-cold acetonitrile with imipramine (100 ng/ml, internal standard). After vortexing and centrifugation at 4° C. for 5 min at 13,000 rpm, the clear supernatant was collected, transferred to liquid chromatography (LC) vials, and analyzed by LC-MS/MS (Agilent 6460) for the quantification of the chemicals.

Statistical analysis. All values are expressed as the means±s.e.m. of ≥3 independent experiments performed in triplicate. Unless indicated otherwise, Two-tailed Student's t-test was used to compare values between two groups. One-way ANOVA with Tukey's test was used to compare values between multiple groups. Two-way repeated-measures ANOVA with Bonferroni's post-hoc test was employed to compare multiple repeated measurements between groups. When there are no values, two-way ANOVA using the linear mixed model was used. P values <0.05 were considered to represent statistically significant differences.

Example 1. Synthesis of MSL Compound of Formula 1

The compound of formula 1 was purchased from Chembridge (Cas No. 831243-88-0).

Example 2. Preparation of 2-(2-chlorophenyl)-5-methoxy-4-(phenylsulfonyl) oxazole (Compound of Formula 2: MSL-7)

Example 2-1. Preparation of methyl 2-(phenylsulfonyl) acetate

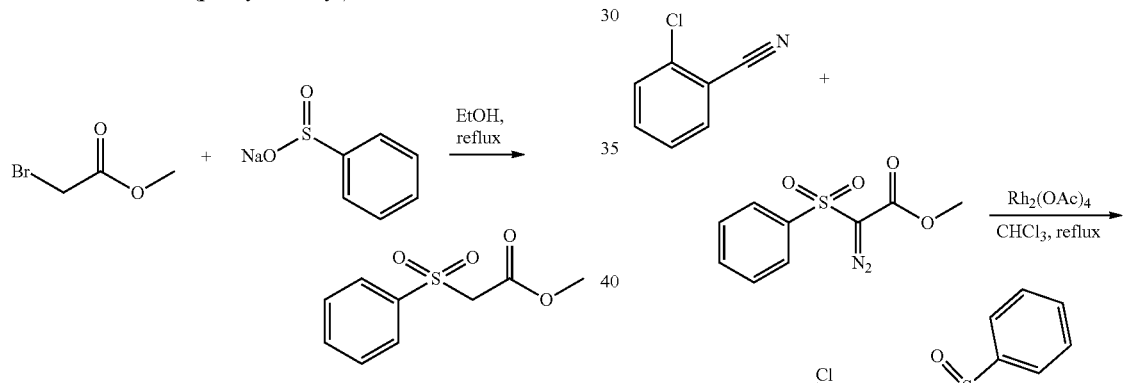

A solution of methyl bromoacetate (10 g, 65.38 mmol) and benzenesulfinic acid, sodium salt (1/9 g, 78.4 mmol) in ethanol (200 ml) was refluxed overnight. Then excess solvent was removed under reduced pressure. The mixture was dissolved in dichloromethane (400 ml) and washed with water (2×200 ml) and brine (150 ml). The organic layer was dried over anhydrous Na$_2$SO$_4$ and concentrated under reduced pressure to give title compound (13.5 g, 96%). The compound was used in the next step without further purification.

Example 2-2. Preparation of methyl 2-diazo-2-(phenylsulfonyl) acetate

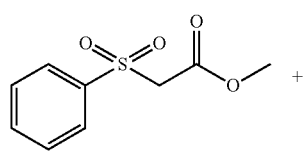

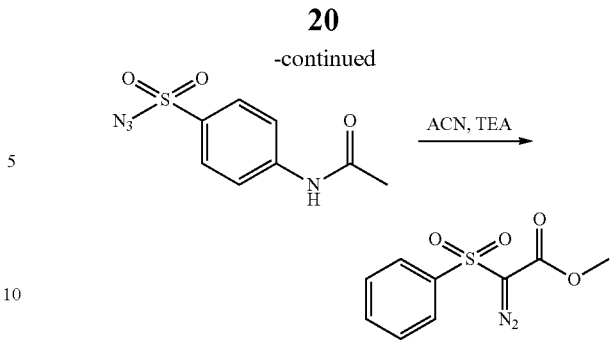

To a stirred solution of methyl 2-(phenylsulfonyl) acetate (13.5 g, 67.7 mmol) and 4-acetamidobenzenesulfonyl azide (16.65 g, 69.31 mmol) in acetonitrile (500 ml) at 0° C., was added triethylamine (7.0 g, 69.3 mmol) dropwise. The reaction mixture was stirred at room temperature for 24 h. The reaction mixture was filtered and washed the obtained solid with ethyl acetate thoroughly. The filtrate was concentrated in vacuo. The resulting residue was purified by column chromatography using ethyl acetate and n-hexane to give the title compound as a pale yellow solid (15 g, 99%).

Example 2-3. Preparation of 2-(2-chlorophenyl)-5-methoxy-4-(phenylsulfonyl) oxazole

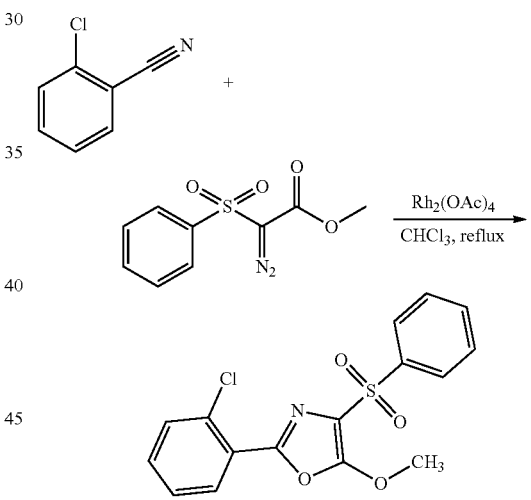

To a refluxing solution of 2-chlorobenzonitrile (600 mg, 4.36 mmol) and rhodium(II) acetate (38.55 mg, 0.087 mmol) in chloroform (10 ml) was added a solution of methyl 2-diazo-2-(phenylsulfonyl) acetate (1.15 g, 4.8 mmol) in chloroform (10 ml). After the addition was finished, the reaction mixture was maintained under reflux condition for 3 h. Reaction mixture was cooled and concentrated under reduced pressure. The residue was purified by column chromatography to afford title compound as a white solid (1.4 g, 92%) $^1$H NMR (300 MHz, DMSO-d$_6$): δ 7.99-7.87 (m, 3H), 7.76-7.59 (m, 4H), 7.58-7.44 (m, 2H), 4.25 (s, 3H).

Example 3. Screening of Autophagy Enhancers without mTOR Inhibition

For this, HEK 293 cells were transfected with pRLuc (C124A)-LC3 (wt) or pRLuc(C124A)-LC3(G120A). G120A substitution of LC3 confers resistance to proteolytic cleavage which is essential for formation of LC3-I and -II, and thus inhibits autophagosomal localization of LC3 (Faskas, T et al. (2009) Identification of novel autophagy regulators by a luciferase-based assay for the kinetics of autophagic flux. Autophagy 5, 1018-1025, while C124A substitution of pRLuc reduces autophagy-independent turnover of RLuc (Faskas, 2009 ibid; Loening, A M et al. Protein Eng Des Sel 19, 391-400).

Figure 1B:
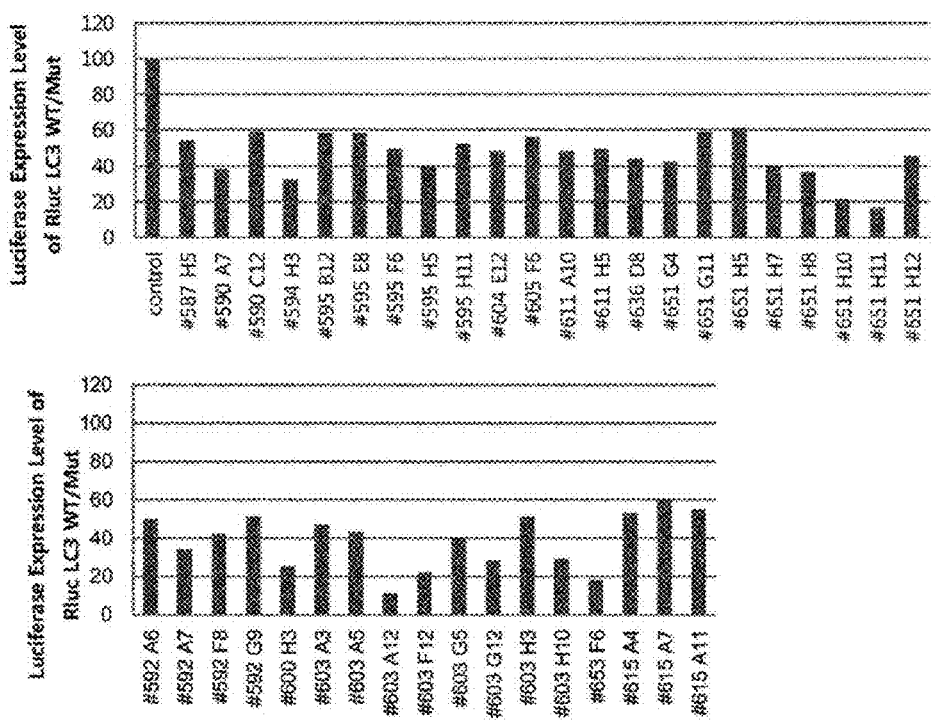
FIG. 1B indicates the results in which HEK 293 cells were transfected with pRLuc(C124A)-LC3 (wt) or pRLuc(C124A)-LC3(G120A), and then the cells were treated with 50 μM of the compounds screened for 6 hrs. The ratio of wt/G120A is indicated as a percent relative to the value from the non-treated control.

Then the transfectants were treated with a chemical library comprising 7,800 purchased chemicals (Korea Chemical Bank) and selected chemicals that reduced wild/mutant normalized luciferase ratio to <0.6 at the concentration of 50 μM without apparent cellular toxicity (viability, >80%). After screening twice, we chose 39 candidate chemicals showing reproducible autophagy-enhancing activity (FIG. 1A and FIG. 1B).

Figure 1C:
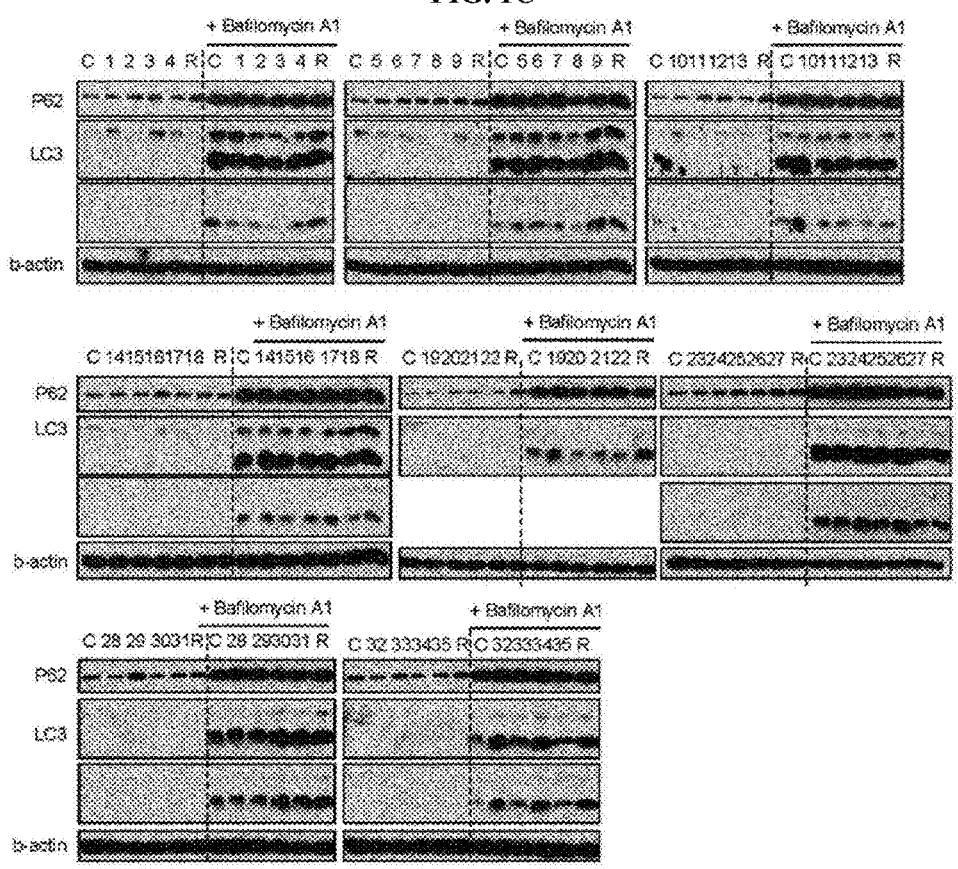
FIG. 1C indicates the results in which the cells treated with the compounds were lysed and analyzed by immunoblotting using the indicated antibody.
Figure 1D:
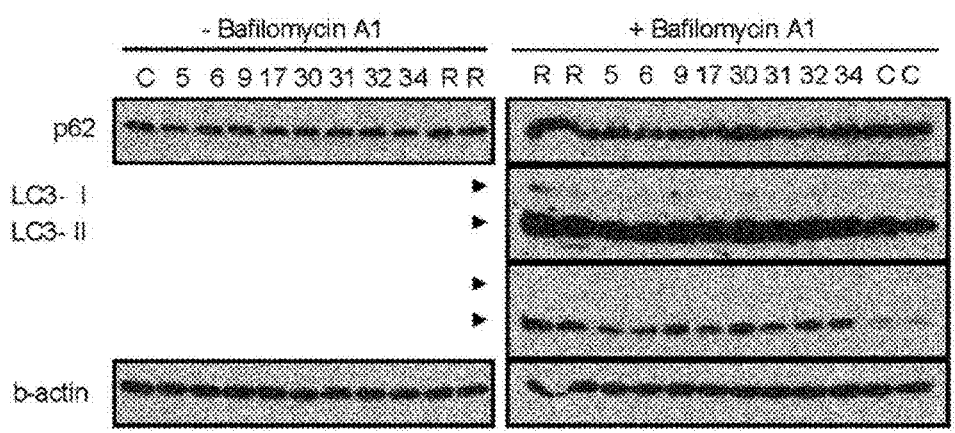
Figure 1E:
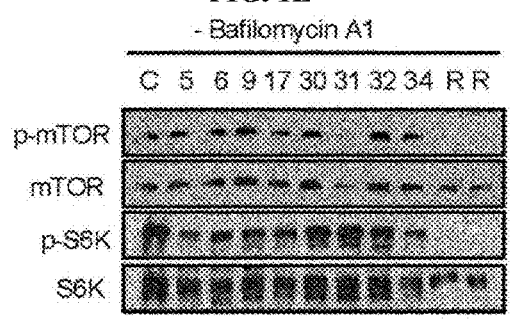

Next, we confirmed autophagy enhancing activity by Western blot analysis (using SK-Hep1 cells). Sixteen chemicals among 39 induced increased LC3-I to -II conversion in the presence of bafilomycin (FIG. 1C). This suggests that they are authentic autophagy enhancers that are capable of increasing autophagic flux. They also decreased p62 in the absence of bafilomycin (FIG. 1C).

Next, we studied whether those autophagy enhancers could inhibit mTOR activity because we wanted to eliminate mTOR inhibitors that can have deleterious effects on metabolic profile and pancreatic β-cell function. For this, we conducted Western blot analysis and found that 8 among 16 chemicals did not inhibit (serum-induced) S6K1 phosphorylation while enhancing autophagic flux (Fig. E). This suggests that they induce autophagic activity in an mTOR independent pathway.

Figure 2A:
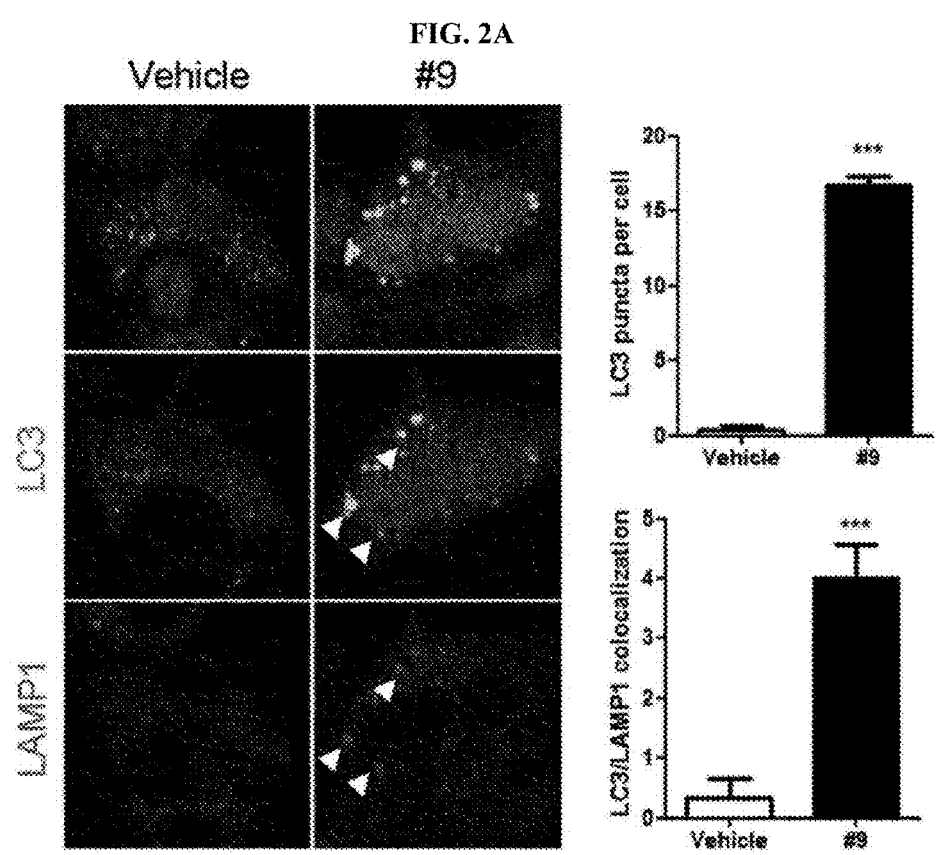
FIG. 2A indicates the results of the experiments in which HeLa cells transfected with RFP-LC3 plasmid for 48 hrs were treated with compound MSL of the present disclosure or vehicle control for 1 hr, which were then immunoblotted with antibody against LAMP1. The arrows indicate puncta. LC3 or the number of puncta was also indicated as bar graph.
Figure 2B:
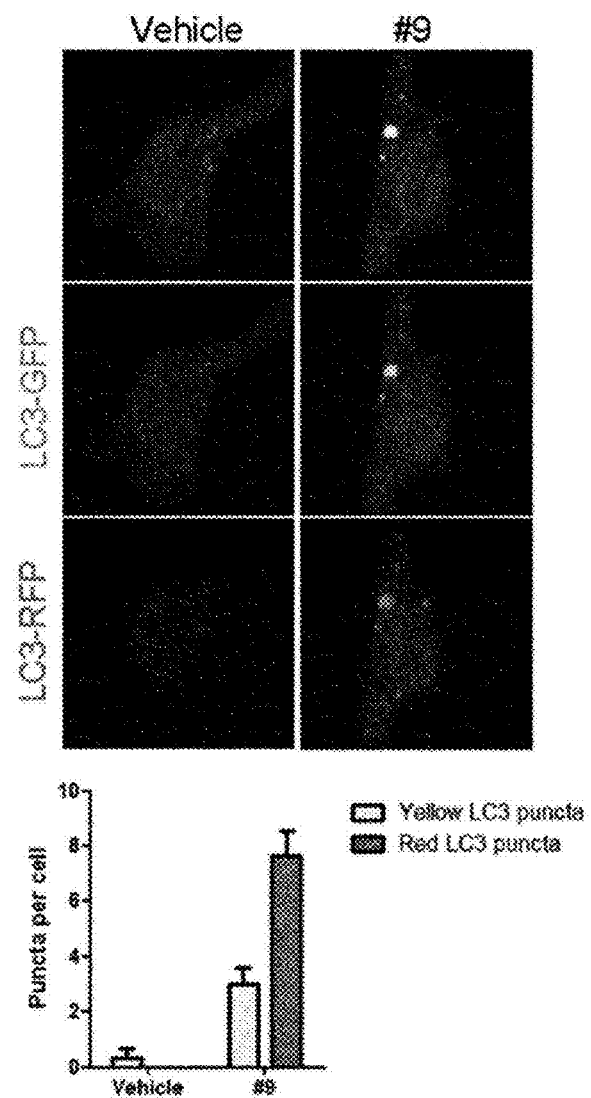
FIG. 2B indicates the results of the experiments in which HeLa cells transfected with mRFP-GFP-LC3 plasmid for 48 hrs were treated with compound MSL of the present disclosure or vehicle control for 1 hr, in which autophagosome (yellow puncta) or autophagolysosome (red puncta) were measured using Image J software. The number of puncta was indicated as bar graph.
Figure 2C:
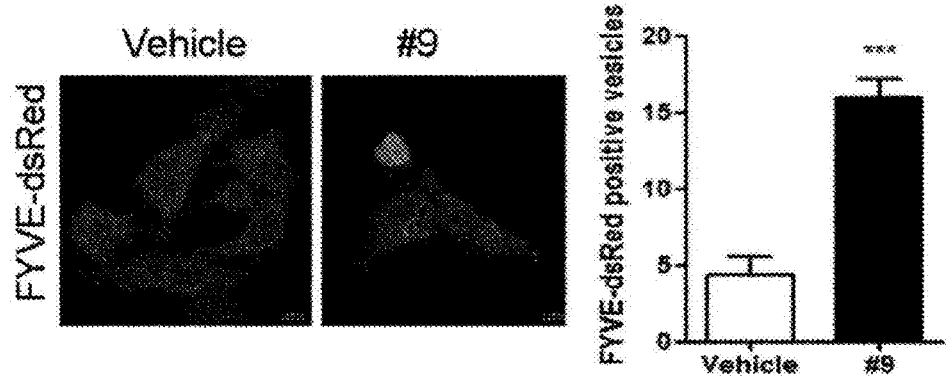
FIG. 2C indicates the results of the experiments in which HeLa cells transfected with FYVE-dsRed plasmid for 48 hrs were treated with compound MSL of the present disclosure or vehicle control for 1 hr, in which the number of FYVE-dsRed vesicles was measured. The measured value were average of the values obtained from at least 3 images. Error bars, S.D. , P<0.01; *, P<0.001. The results indicate that MSL compound according to the present disclosure increases the autophagic flux.

To further confirm increased autophagic flux by chemical MSL, we studied lysosomal events associated with autophagic activity. MSL-induced LC3+ autophagosome were positive for the lysosomal markers LAMP1, showing colocalization autophagic organelles and lysosomes and suggesting the occurrence of lysosomal events in the process of autophagolysosome formation (FIG. 2A). Moreover, confocal microscopy after transfection of tandem mRFP-GFP-LC3B probe showed increases of the number of both yellow puncta (RFP+ GFP+; representing early autophagic organelles) and red puncta (RFP+ GFP−, representing autolysosomes) after treatment with MSL, again confirming the occurrence of lysosomal steps of autophagy (FIG. 2B). We also assessed autophagosome nucleation. Recruitment of FYVE-dsRed+ vesicle was increased by MSL which suggests activation of Vps34 and production of phosphatidylinositol-3-phosphate (PI3P), necessary steps in the formation of autophagosomes (FIG. 2C). Collectively, all these results indicate that MSL enhances autophagy flux.

Figure 3A:
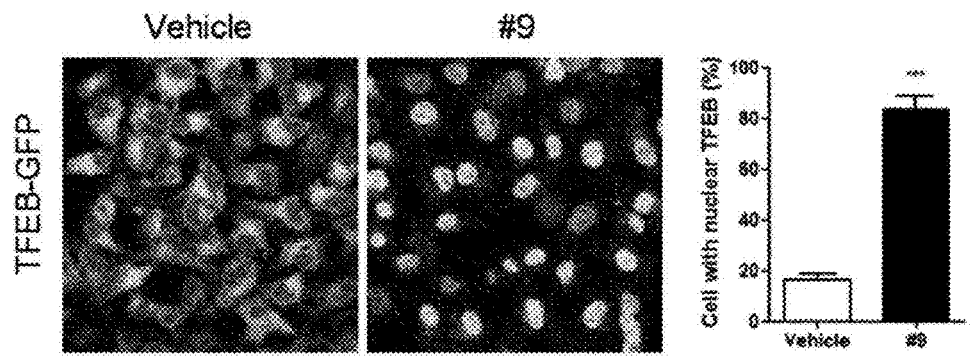
FIG. 3A is the graph showing the percentage of nuclear translocated TFEB for which TFEB-GFP HeLa cells were treated with MSL compound for 4 hrs and then nuclei of the cells were stained with DAPI.
Figure 3B:
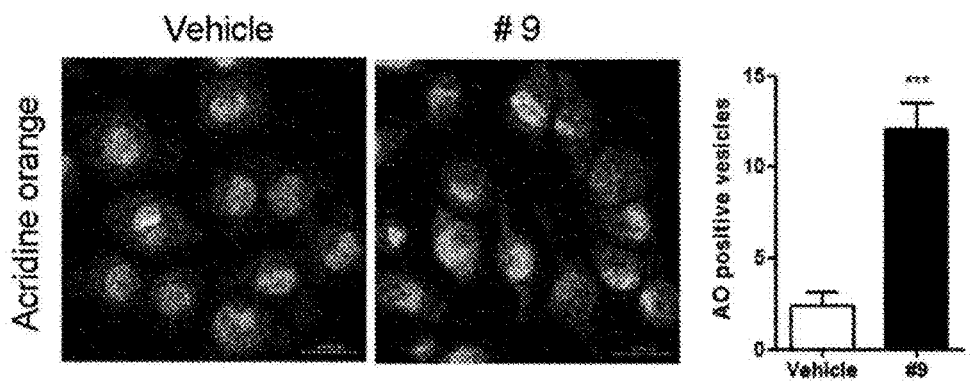
FIG. 3B is the results of the experiments in which HeLa cells were incubated in the presence of MSL compound or vehicle control for 24 hrs and then the acidic vesicular organelles formed were stained with acridine orange.

Example 4. Identification of the Mechanism of Autophagy Activation Focused on Lysosome Next, we investigated the molecular mechanism of autophagy activation by MSL which is unrelated to the inhibition of mTOR activity. We studied lysosomal steps of autophagy which is activated in autophagy activation by MSL. When we examined the changes of TFEB, a key regulator of lysosome biogenesis and autophagy, we observed that TFEB was translocated to the nuclei in the majority of MSL-treated HeLa cells (FIG. 3A). The percentage of nuclei showing TFEB positivity was greatly increased in MSL-treated cells compared to untreated cells (FIG. 3A). Consistent with TFEB translocation, red fluorescence after acridine orange staining was significantly increased, showing enhanced lysosomal acidification and content in MSL-treated cells (FIG. 3B).

Figure 3C:
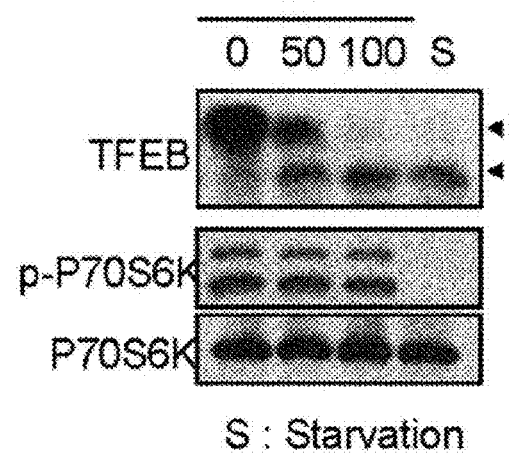
FIG. 3C is the results of the experiments in which TFEB-GFP HeLa cells were treated with MSL compound or vehicle control for 4 hrs and then the cells were immunoblotted with the antibodies indicated.
Figure 3D:
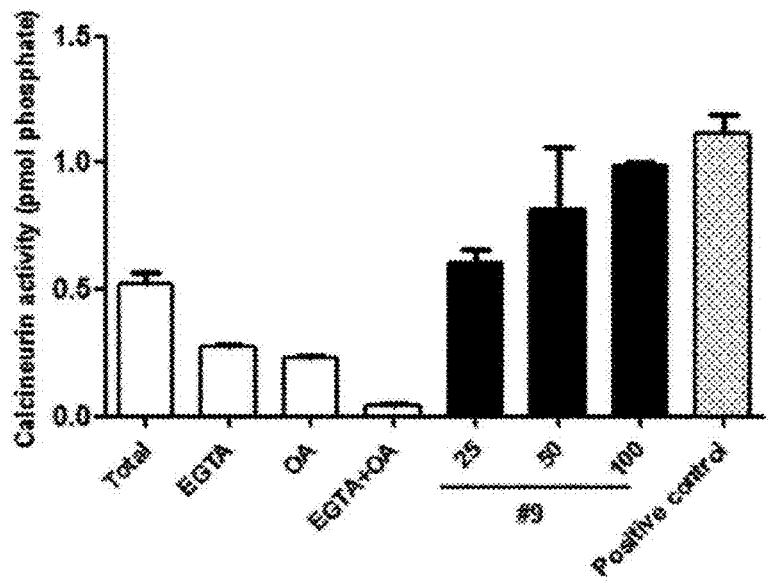
FIG. 3D and FIG. 3E is the result of measuring the calcineurin activity in the lysates of Hepa1c1c7 cells treated with the compounds indicated. Error bars, S.D. , P<0.01;*, P<0.001. The results indicate the mechanism of action showing that the increase of autophagic flux by treatment of the present compound MSL leads to the TFEB control via the activation of calcineurin activation.
Figure 3E:
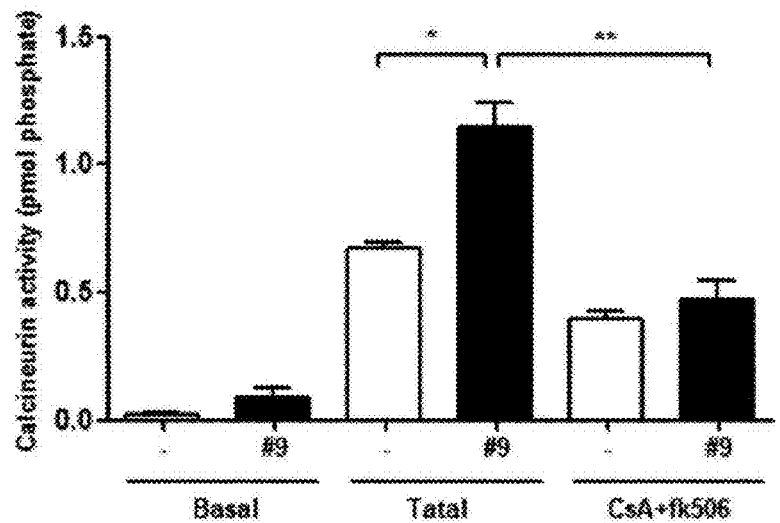
Figure 9:
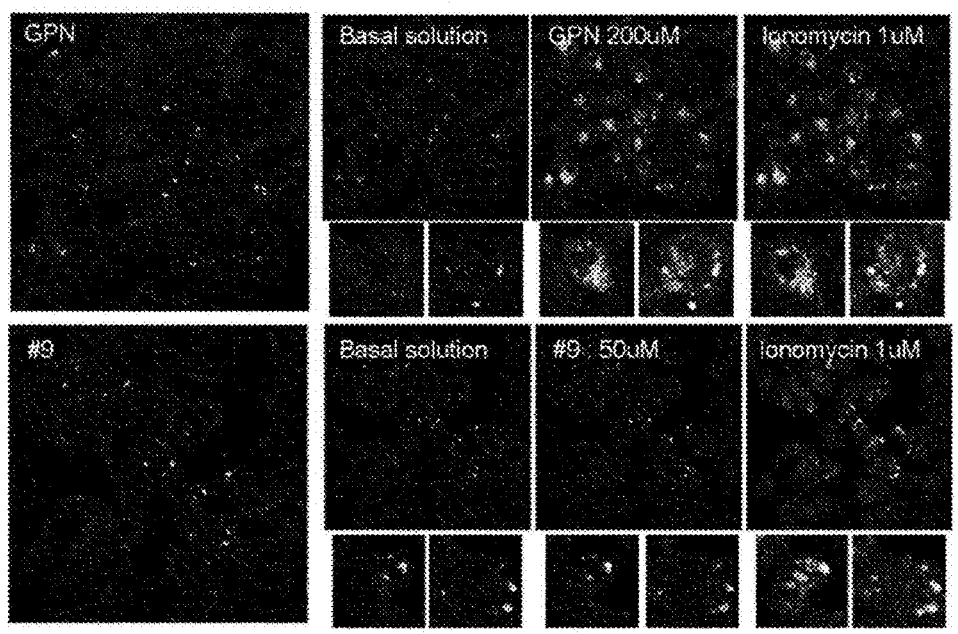
FIG. 9 indicates that MSL compound of the present disclosure does not have an effect on releasing calcium from lysosome. HeLa cells were transfected with perilysosomal GCaMP3-ML1 calcium probe, and Ratiometric image (474 and 410 nm excitation) was obtained. After that, application of GPN (200 μM) induced smaller response. The maximum response was induced by the application of ionomycin (1 μM). This indicates that the regulation of TFEB by the present MSL compound is controlled independently of the calcium release.

We next investigated the mechanism of TFEB translocation by MSL which does not involve mTOR inhibition (FIG. 3C) by studying lysosomal calcium-calcineurin pathway that has been reported to enhance TFEB translocation by dephosphorylating TFEB (Medina, D L et al. (2015) Lysosomal calcium signaling regulates autophagy through calcineurin and TFEB. Nature Cell Biol 17, 288-299). When we tested whether MSL increases the release of lysosomal Ca2+ by transfecting HeLa cells with GCaMP3-ML1, a lysosome-specific Ca2+ probe (Medina, 2015, ibid), we observed no increase of lysosomal Ca2+ release, while a lysosomotropic agent GPN or ionomycin, a calcium ionophore, induced lysosomal Ca2+ release (FIG. 9). Thus, we studied whether MSL increases calcineurin activity regardless of lysosomal Ca2+ efflux. Indeed, an in vitro calcineurin phosphatase assay revealed that calcineurin activity was significantly increased by MSL (FIG. 3D). Furthermore, the increased phosphatase activity was significantly inhibited by cyclosporin A (CsA) or FK506, supporting enhanced calcineurin activity by MSL. Cyclosporin A (CsA) or FK506 also abrogated TFEB translocation by MSL (FIG. 3E), consistent with the role of calcineurin activity in TFEB translocation by MSL. The increased calcineurin activity by MSL was further substantiated by an enhanced TFEB mobility in Western blot analysis (data not shown).

Figure 4A:
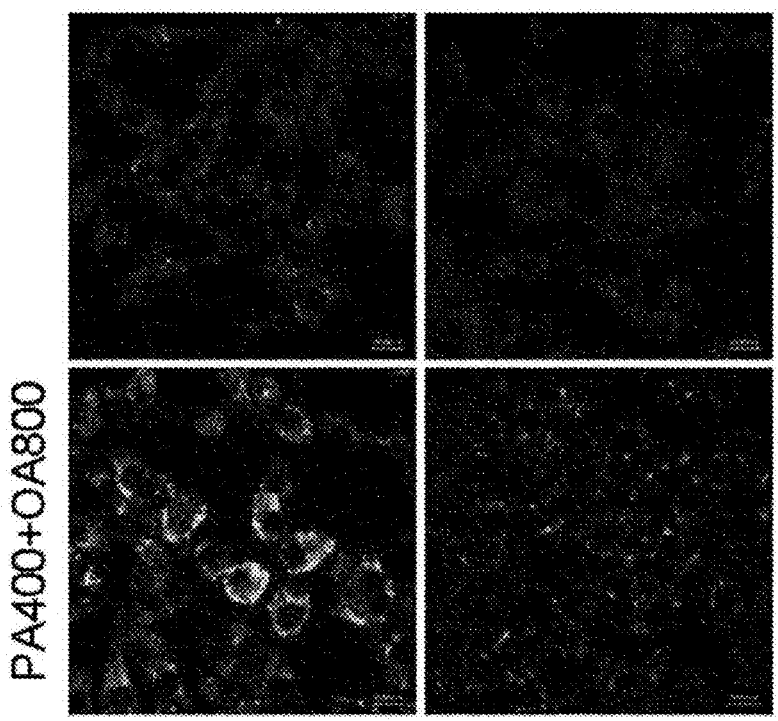
FIG. 4A is the result of the experiments in which HeLa cells were treated with palmitic acid and oleic acid for 16 hrs and then treated with vehicle control or MSL compound for 20 hrs, which were then stained with BODIPY 493/503.
Figure 4B:
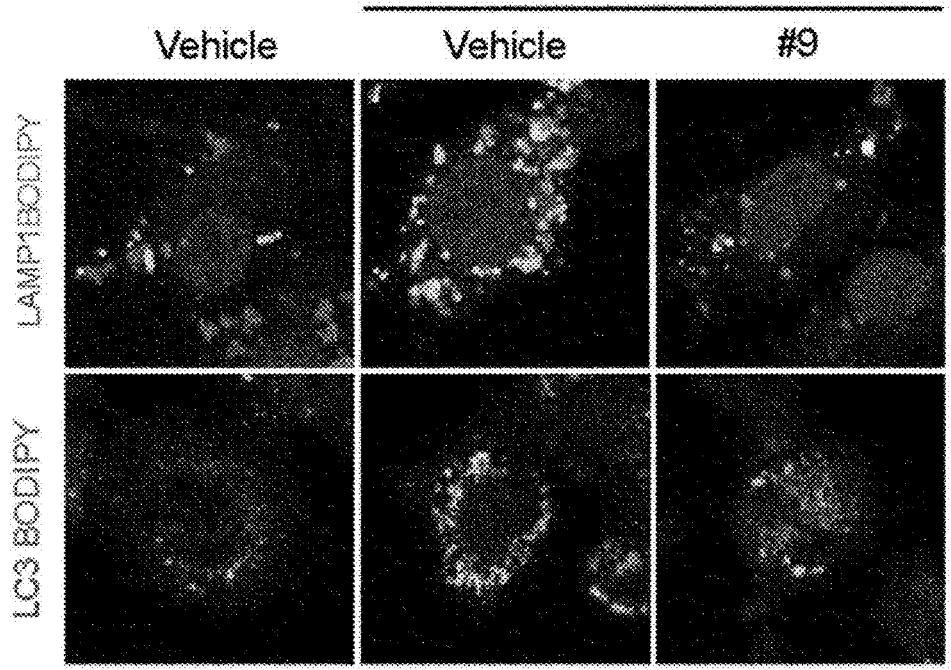
FIG. 4B is the results of the experiments in which the cells of FIG. 4A were stained with LC3 to observe lysosomes, LMAP1 and autophagosomes.
Figure 4C:
FIG. 4C is the result of the experiments in which HeLa cells were treated with palmitic acid and oleic acid for 16 hrs and then treated with compound indicated for 20 hrs, after which the lipid droplets in each cell were quantified by Image J software. The measured value was the average of the values obtained from at least 3 images. Error bars, S.D. , P<0.01; *, P<0.001. The results indicate that the increase in the autophagic flux by the present MSL compound enhances the clearance of the lipid droplets which usually increases in metabolic disease, and thus the metabolic disease can be effectively improved/treated by the present compound.
Figure 4C:
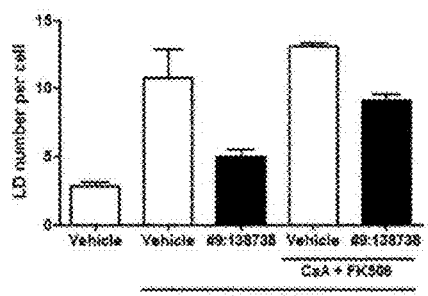
Figure 4C:
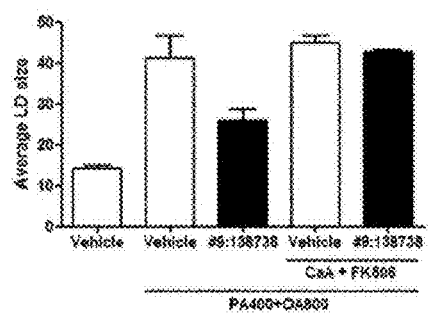

Example 5. Effects of MSL on Lipid Metabolism and Inflammasome Activation In Vitro We next investigated whether MSL is able to affect cellular metabolism. We loaded Hepa1c1c7 cells (ATCC CRL 2026™) with PA and OA and examined whether MSL enhances clearance of lipid droplets. Compared with untreated ontrols, cells treated with MSL for 16 h showed significantly decreased content of lipid droplets stained BODIPY (FIG. 4A). Furthermore, LC3 or LAMP1 with BODIPY was colocalized with BODIPY (FIG. 4B), confirming a direct interaction between autophagolysosomes and intracellular lipids. Consistent with the lipid staining, lipid content in cells loaded with PA (Palmitic acid) and OA (Oleic acid) was significantly reduced by MSL (FIG. 4C). These results indicate that MSL increased lipid turnover probably by activating autophagy or lipophagy through enhancement of calcineurin activity, and suggest the possibility that MSL may improve metabolic profile associated with lipid overload or obesity.

Figure 5A:
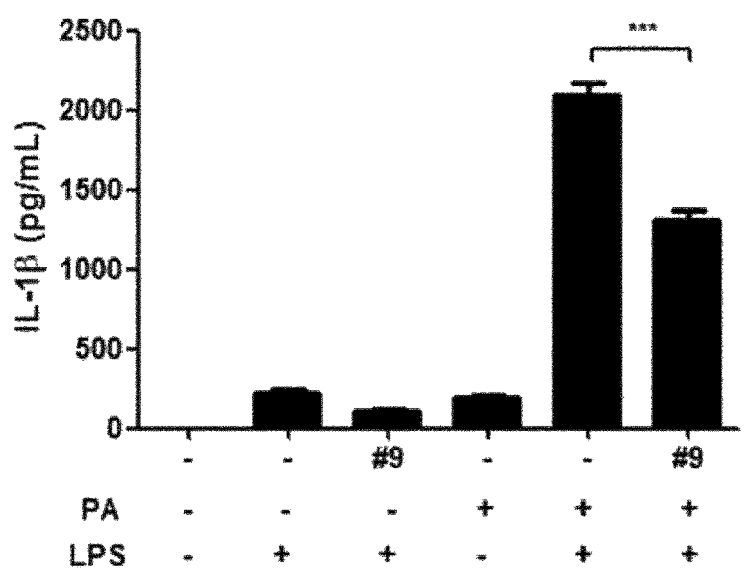
FIG. 5A is the results of the experiment in which primary peritoneal macrophages were isolated and treated with palmitic acid, LPS and MSL and then the concentration of IL-beta was measured from the supernatant using ELISA. Error bars, S.D. , P<0.01; *, P<0.001, two-way ANOVA.

Inflammasome activation through NLRP3 is an important component of metabolic inflammation associated with insulin resistance in obesity, and lipids such as palmitic acid (RA) act as ligands for NLRP3 (Vandanmagsar, B et al. (2011) The NLRP3 inflammasome instigate obesity-induced inflammation and insulin resistance. Nat Med 15, 179-188). Furthermore, NLRP3 activation is modulated by autophagy which regulates not only nutrient status or organelle function but also innate or adaptive immunity (Levine et al., Unveiling the roles of autophagy in innate and adaptive immunity. Nature Review Immunology 7:767-777, 2007). When we treated macrophages (MΦs) with PA in combination with lipopolysaccharide (LPS), release of IL-1β measured by ELISA was significantly decreased in MSL treated macrophages than that from untreated macrophages (FIG. 5A), suggesting decreased lipid-induced inflammasome activation by MSL. Western blot analysis also showed decreased caspase-1 cleavage and IL-1 β maturation by MSL, confirming the results from IL-1 β measurement (data not shown).

Figure 5B:
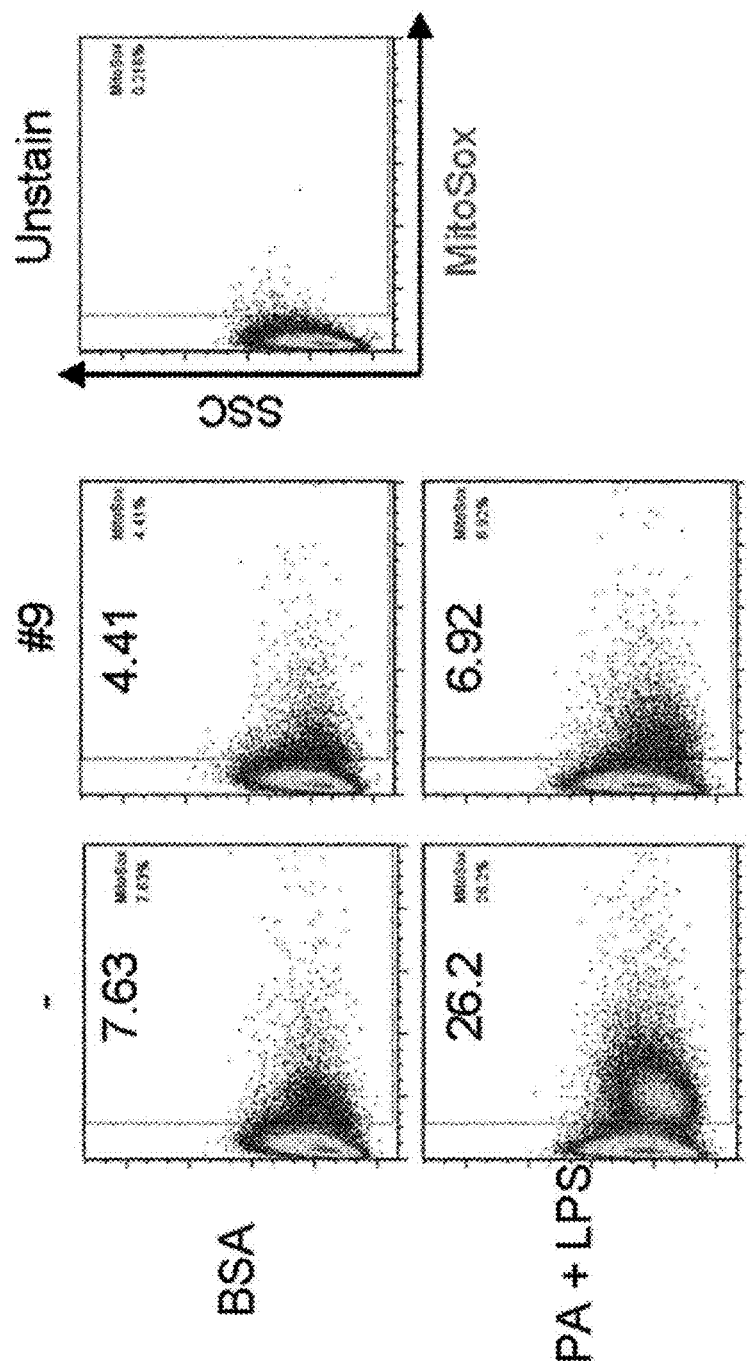

Since previous papers reported that autophagy modulates inflammasome activation by controlling turnover of dysfunctional mitochondria acting as a hub organelle for inflammasome activation (Misawa, T et al. (2013) Microtubule-driven spatial arrangement of mitochondria promotes activation of the NLRP3 inflammasome. Nat Immunol 14, 454-460). Thus we studied mitochondrial events in cells treated with MSL. When mitochondrial ROS content reflecting mitochondrial dysfunction or damage was measured by MitoSox staining, PA in combination LPS significantly augmented mitochondrial ROS content in MΦs. Here, MSL treatment significantly reduced the mitochondrial ROS content in cells treated with PA plus LPS (FIG. 5B). We also evaluated mitochondrial potential reflecting mitochondrial function. Mitochondrial potential determined by MitoTracker Red staining was significantly decreased MΦs treated with PA plus LPS. Again, MSL treatment significantly reduced mitochondrial potential in cells treated with PA plus LPS (FIG. 5C).

These results suggest that MSL reduces inflammasome activation by decreasing content of lipids acting as ligands of inflammasome activation and improving mitochondrial function in cells with lipid overload.

Example 6. Metabolic Improvement In Vivo by MSL

Figure 6A:
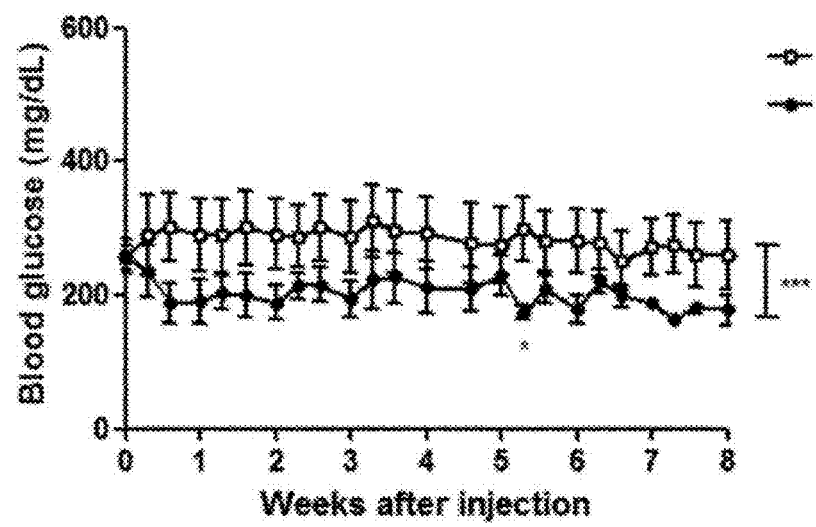
FIG. 6A and FIG. 6B each indicates the fasting blood sugar and the body weights respectively from ob/ob mice which were treated with vehicle control or (50 mg/kg/2 days) for 8 weeks.
Figure 6B:
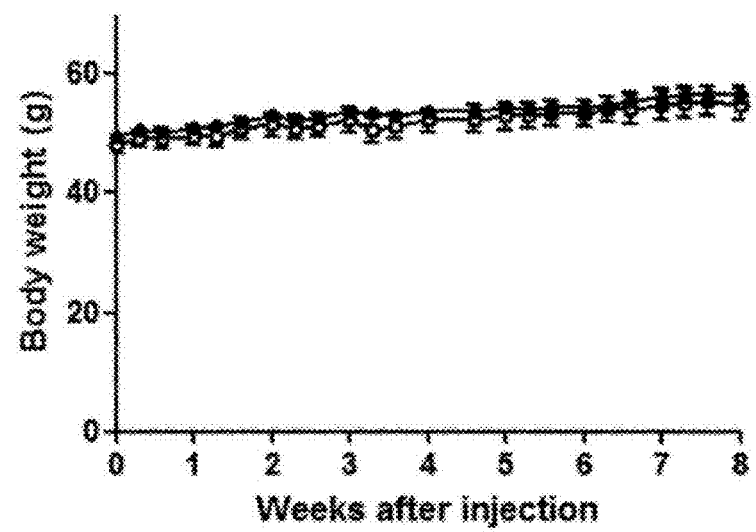
Figure 6C:
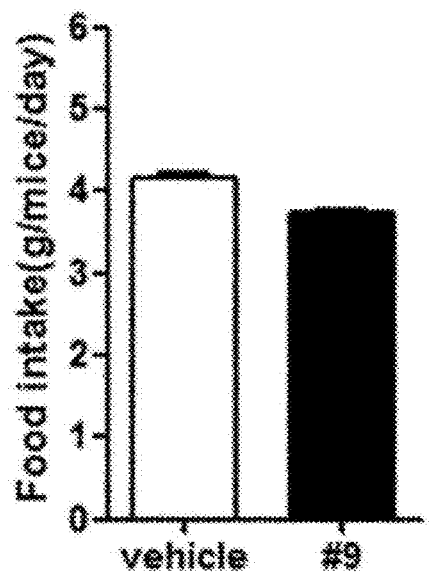
FIG. 6C indicates the amount of feed intake from ob/ob mice which were treated with vehicle control or for 8 weeks.

We next studied whether MSL can activate autophagic flux in vivo. When we administered MSL after pretreatment with leupeptin (Ueno, T et al. (1991) Membrane markers of endoplasmic reticulum preserved in autophagic vacuolar membranes isolated from leupeptin-administered rat liver. J Biol Chem 266, 18995-18999), LC3-I to -II conversion was increased in the liver, supporting that MSL can increase autophagic flux in vivo. We next studied whether MSL administration can improve metabolic profile associated with obesity. We treated ob/ob mice with MSL at 50 mg/kg for 8 weeks. Food intake and body weight were not affected by administration of MSL, however, non-fasting blood levels were significantly decreased in those mice compared to control treated ob/ob mice (FIG. 6A, FIG. 6B).

Figure 6D:
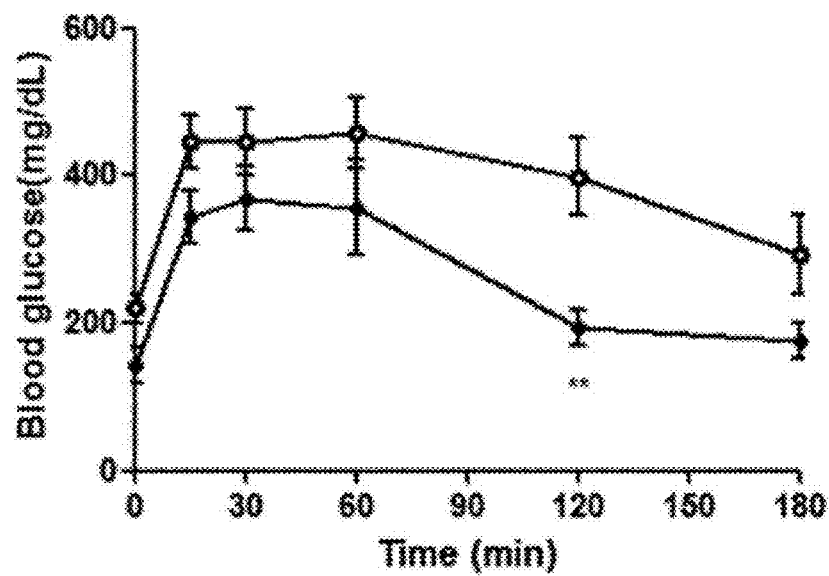
FIG. 6D and FIG. 6E each indicates the IPGTT results and AUC value measured after the 8 week administration.
Figure 6E:
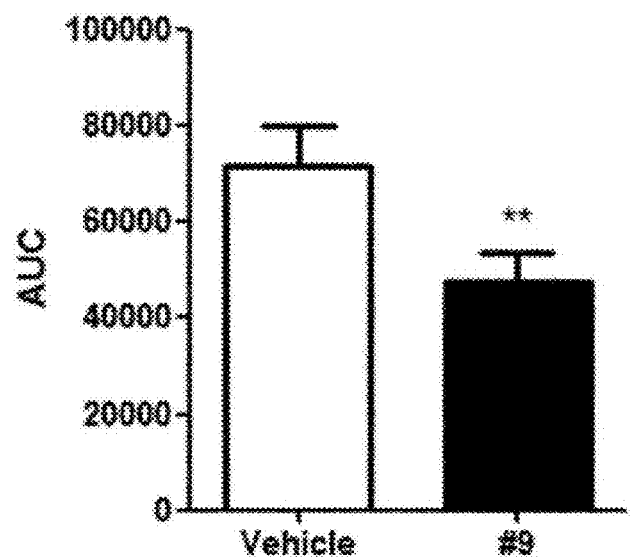
Figure 6F:
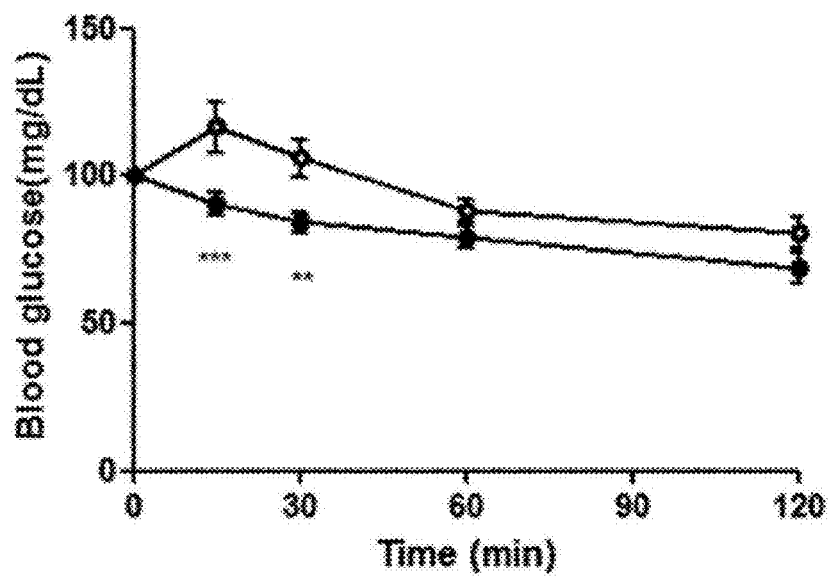
FIG. 6F and FIG. 6G indicates the ITT results and AUC value measured after the 8 week administration.
Figure 6G:
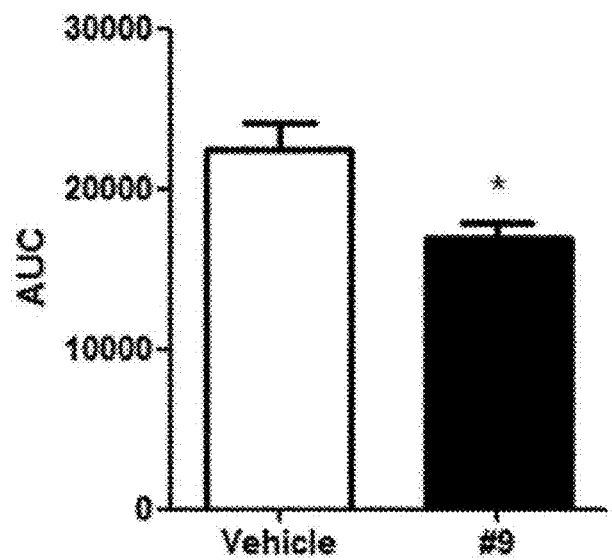
Figure 6H:
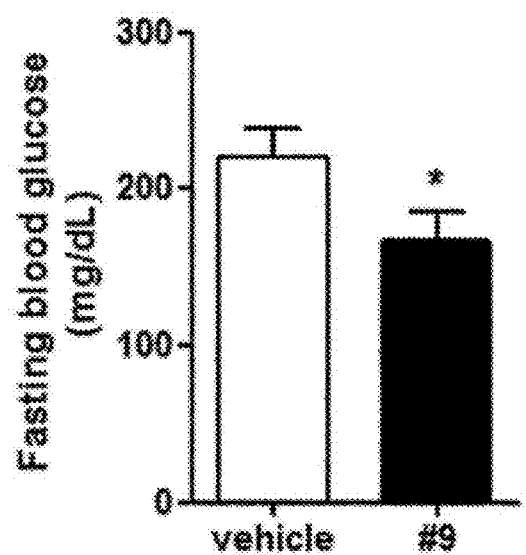
FIG. 6H indicates the fasting blood sugar after the 8 week administration.
Figure 6I:
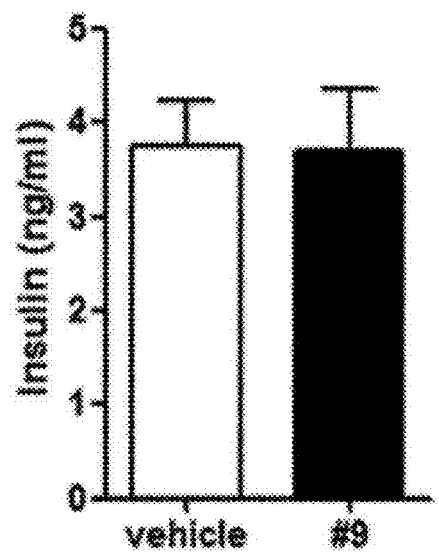
FIG. 6I indicates the concentration of insulin after the 8 week administration.
Figure 6J:
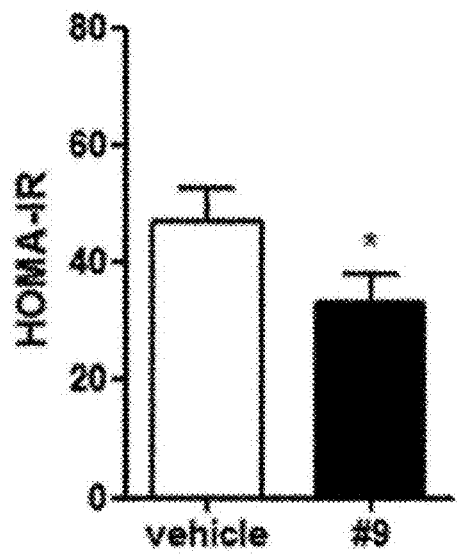
FIG. 6J indicate the result of HOMA-IR measured after the 8 week administration.
Figure 6K:
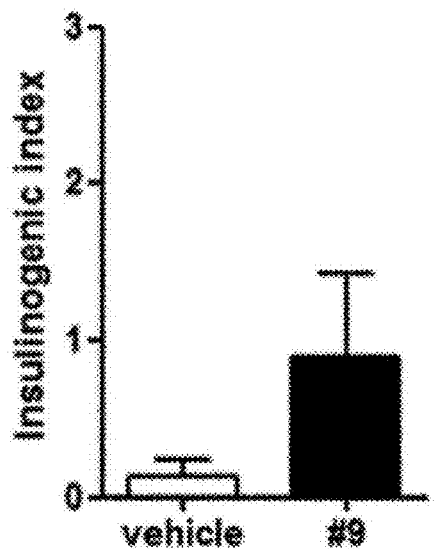
FIG. 6K indicates the results the Insulinogenic index measured after the 8 week administration. Error bars, S.D. *, P<0.05; , P<0.01; *, P<0.001. Students t-test and one-way ANOVA. The results indicates that the present compound MSL can be advantageously used to effectively treat metabolic disease by improving the metabolic parameter in disease model mouse.
Figure 7A:
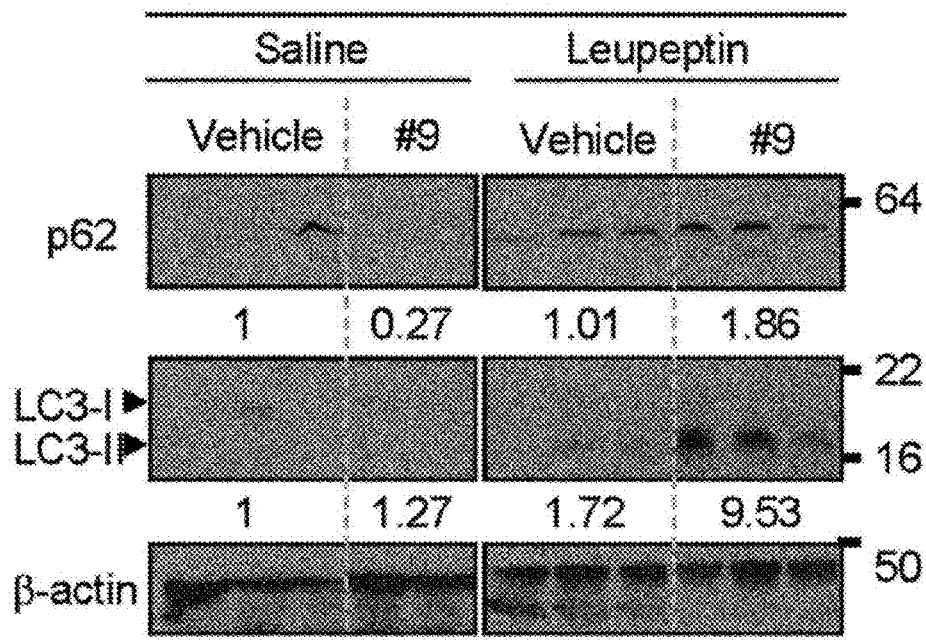
FIG. 7A is the result of the experiment in which ob/ob mice were peritoneally injected with 30 mg/kg leupeptin and then after 1 hr, vehicle control or MSL compound were peritoneally administered. Three hours post administration, the liver lysates were prepared and immunoblotted. The numbers above the bands indicates fold changes normalized to beta actin bands.
Figure 7B:
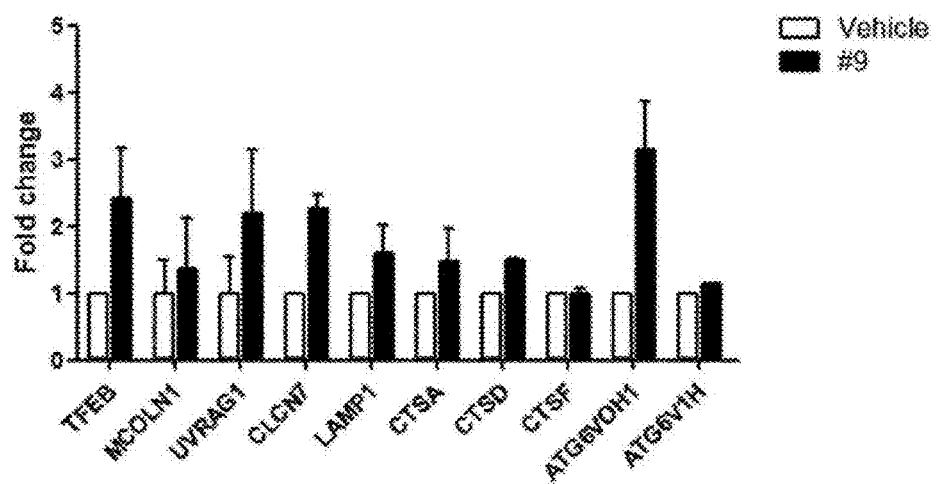
FIG. 7B indicates the concentration of mRNA of TFEB related genes measured by performing RT-PCT using a total RNA isolated from liver sample treated same as above except that Leupeptin was not administered. The values represent mean±S.D of fold changes compared to control mice (vehicle control) obtained from three mice. The results indicate that the enhancement of the metabolic parameter is related with the increase of autophagy.

Fasting blood glucose levels was also significantly improved by MSL administration for 8 weeks (FIG. 6H). Furthermore, IPGTT and ITT showed significant improvement of glucose tolerance and insulin sensitivity, respectively (FIG. 6D, 6F), which was accompanied by reduced AUC (FIG. 6E, 6G). HOMA-IR index representing insulin resistance was also slightly decreased in MSL treated mice compared with control mice (FIG. 6J). Improved metabolic profile after 8 weeks of MSL administration was accompanied by increased autophagic activity in the liver measured after leupeptin administration (FIG. 7A). Of note, gene expression analysis showed that the expression of TFEB-regulated genes was significantly higher in MSL treated mice compared to controls (FIG. 7B), consistent with nuclear translocation of TFEB by MSL treatment of cells in vitro.

Figure 8A:
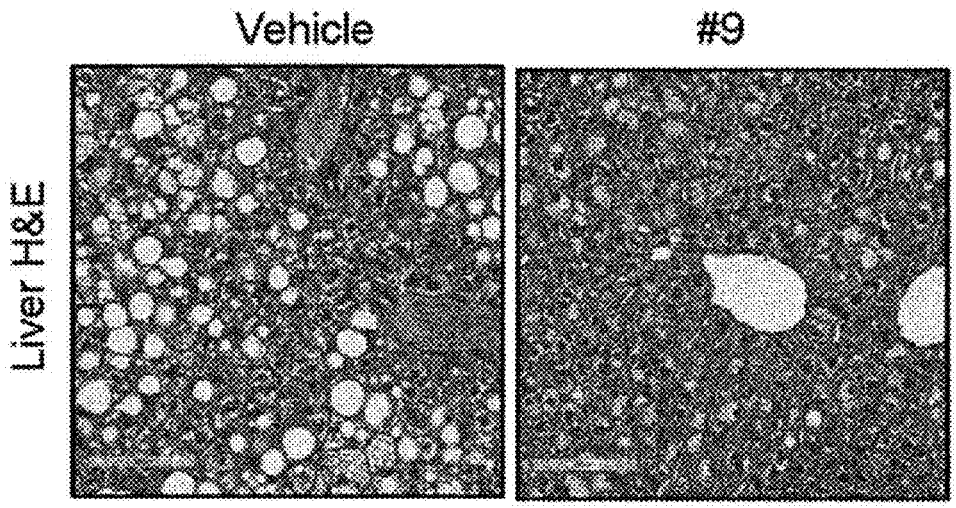
FIG. 8A is the result of Hematoxylin-Eosin stained liver section from ob/ob mice treated with MSL compound or vehicle for 8 weeks.
Figure 8B:
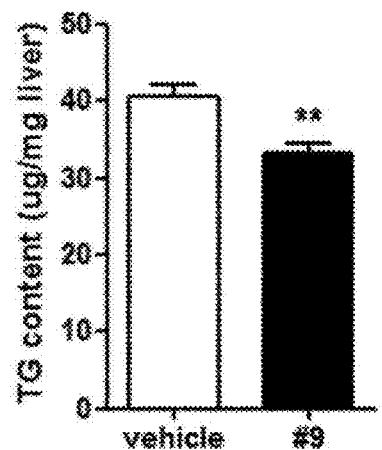
FIG. 8B is the result of measuring the concentration of TG using free glycerol reagent containing lipase in the lipid sample extracted using a mixture of chloroform/ethanol from the liver of ob/ob mice.
Figure 8C:
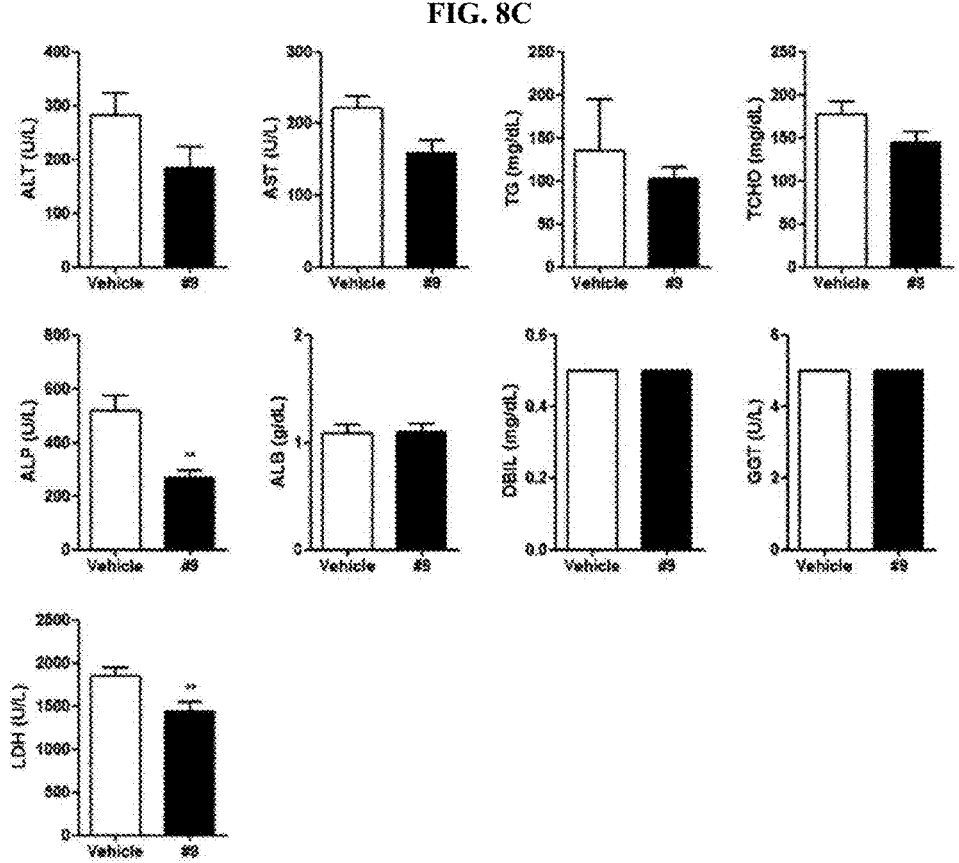
FIG. 8C is the result of blood chemistry profile analyzed using chemical analyzer from serum sample obtained from ob/ob mice treated with MSL compound or vehicle for 8 weeks.
Figure 8D:
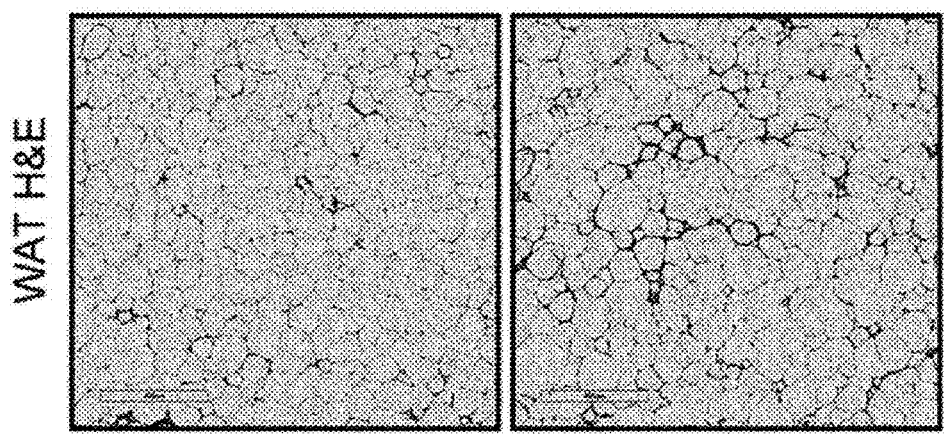
FIG. 8D is the result of Hematoxylin-Eosin stained white adipose tissue section from ob/ob mice treated with MSL compound or vehicle for 8 weeks.
Figure 8E:
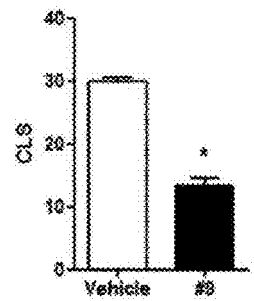
FIG. 8E is the immuno-stained result of F4/80+ cells from white adipose tissue (left) and the quantification result of adipose cell F4/80+ CLS (right) indicated as a frequency of CLS (crown-like structures) in the white adipose tissue of the mice as described above.
Figure 8F:
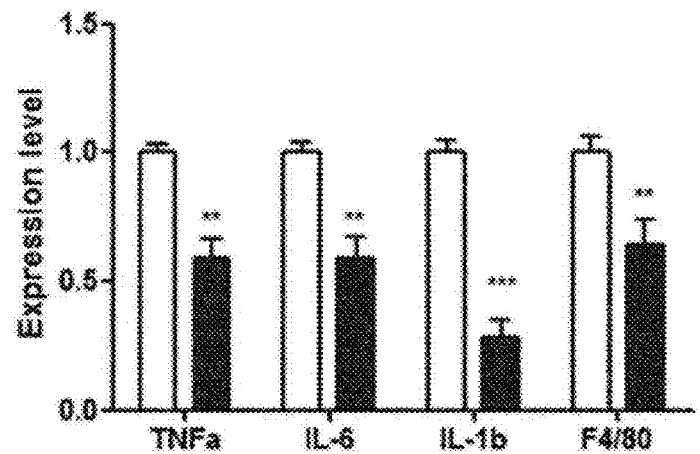
FIG. 8F is the result of quantifying the expression of WAT gene from the mice as described above using RT-PCR. Error bars, S.D. *, P<0.05; , P<0.01; *, P<0.001. The results indicate that the increase of the autophagic flux by MSL of the present disclosure improves the removal of lipid droplet that are increased in metabolic disease, thus indicating that the present compound can be effectively used for treating or improving metabolic disease.

We next studied possible improvement of fatty liver associated with obesity. Treatment with MSL for 8 weeks apparently reduced accumulation of lipid droplets in the liver of ob/ob mice (FIG. 8A). Oil Red O staining confirmed decreased lipid content in ob/ob mice treated with MSL compared to control mice (data not shown). Serum ALT/ASL levels were also significantly reduced by MSL treatment for 8 weeks (FIG. 8C), suggesting decreased fatty liver damages. We also examined changes of metabolic inflammation that plays an important role in insulin resistance associated with obesity in these mice. In WAT of mice treated with MSL for 8 weeks, the number of crown-like structures (CLSs), macrophage aggregates around dead adipocytes reflecting the severity of metabolic inflammation, was significantly decreased compared with control mice (FIG. 8D, E), indicating improved metabolic inflammation by MSL. Real-time RT-PCR also demonstrated significantly reduced expression of inflammatory markers such as Tnfa, I-16, II-1β and F4/80 (FIG. 8F), confirming reduced metabolic inflammation by MSL treatment of obese mice.

Figure 10:
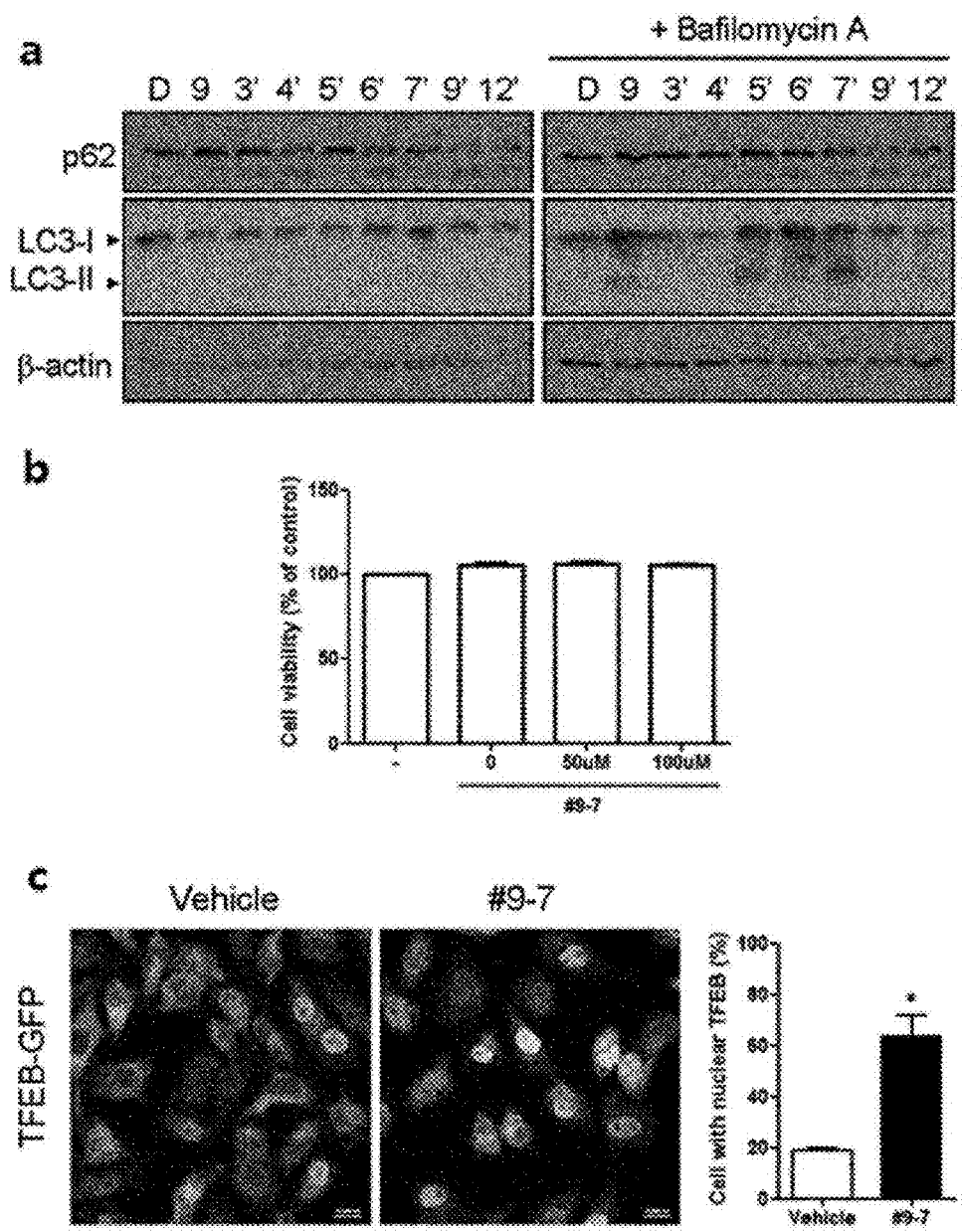
FIG. 10 is the result of the experiments using compound of formula 2 (hereinafter referred to as MSL-7) of the present disclosure as an autophagic enhancer.
Figure 11A:
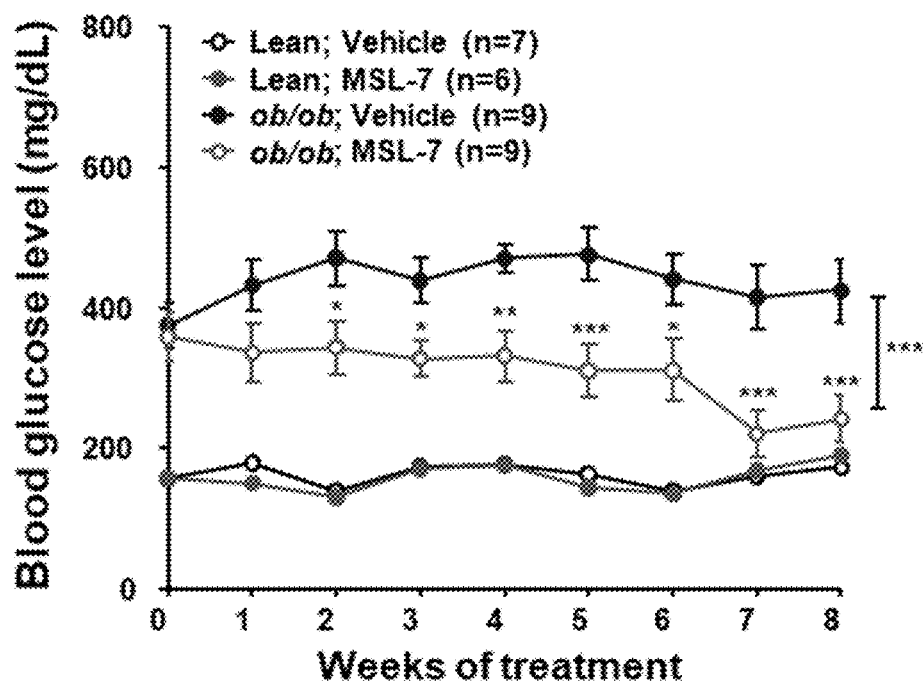
FIG. 11A is the result of fasting glucose concentration of ob/ob mice administered with vehicle control or MSL-7 (50 mg/kg/2 days) for 8 weeks.
Figure 11B:
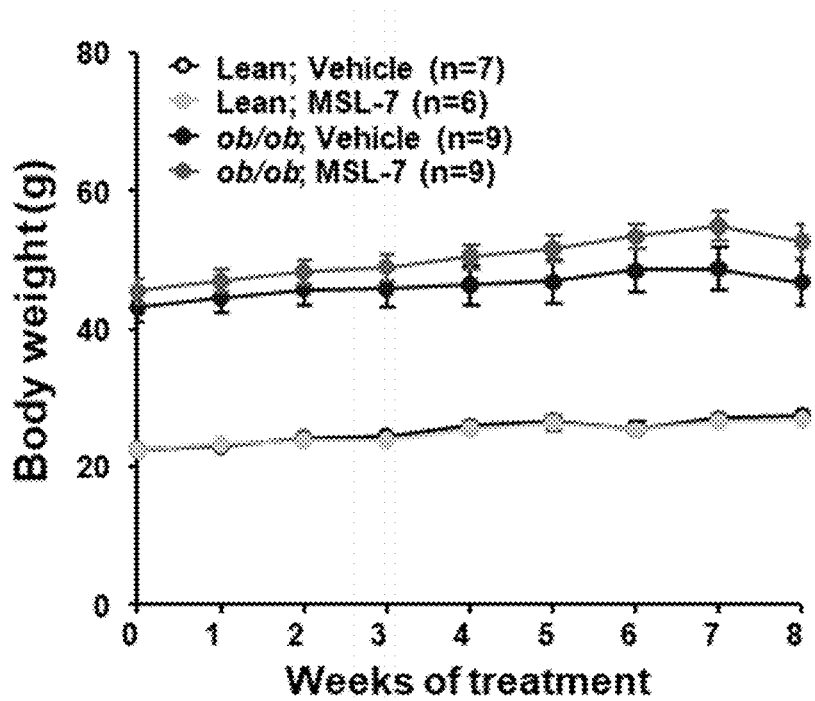
FIG. 11B is the body weight monitored of the mice of FIG. 11A.
Figure 11C:
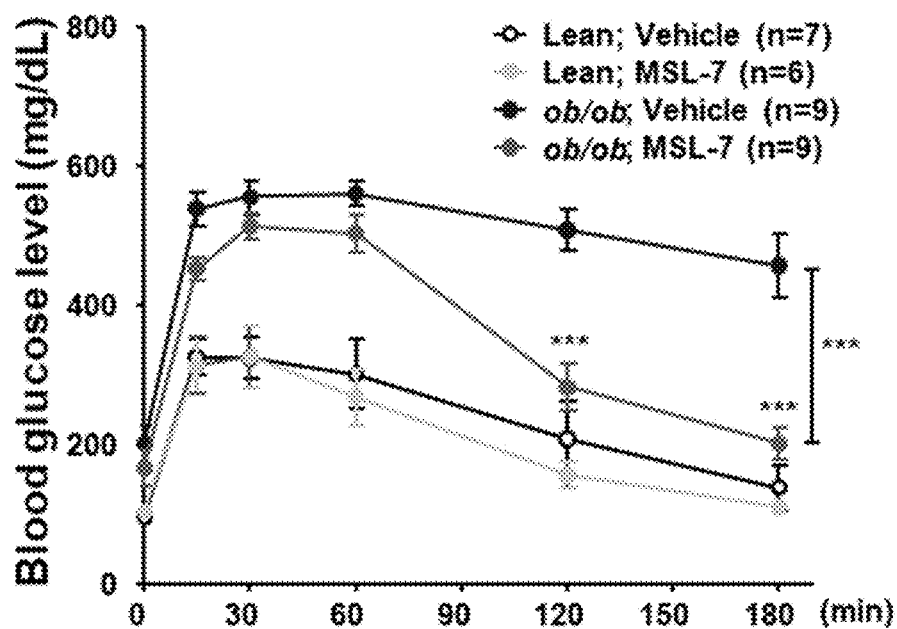
FIG. 11C is the result of experiments performed at 8 weeks after the administration of IPGTT (FIG. 1 IC) and ITT (FIG. 11D).
Figure 11D:
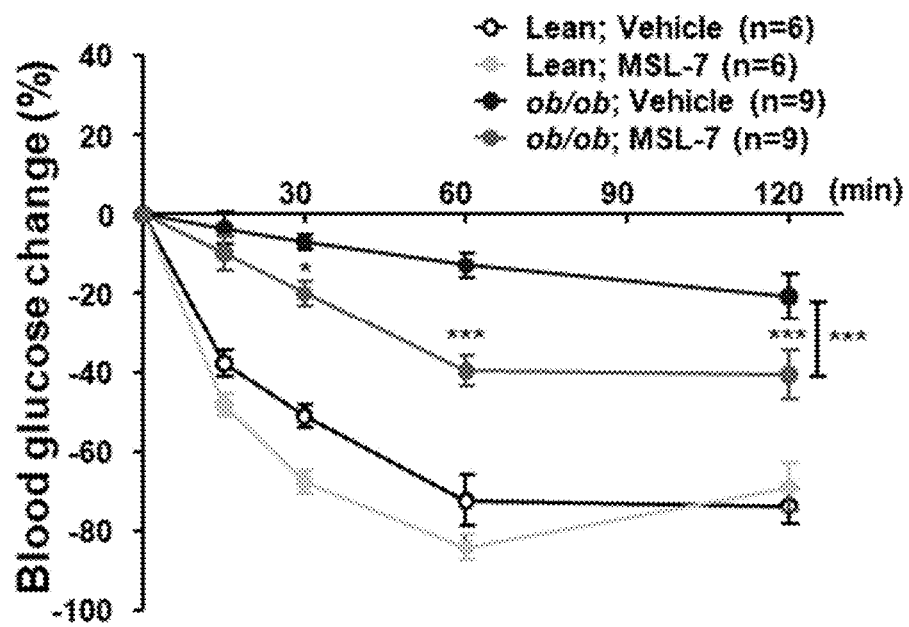
FIG. 11 indicates that compound of formula 2 of the present disclosure (hereinafter referred to as MSL-7) improves the metabolic parameters of ob/ob mice.
FIG. 11E is the results of measuring blood chemistry profile of the ob/ob mice administered with vehicle control or MSL-7 compound for 8 weeks using chemical analyzer. Error bars, S.D. *, P<0.05; , P<0.01; *, P<0.001. Students t-test and one-way ANOVA. The results indicate that MSL is more effective than its derivative MSL-7 in improving the metabolic disease due to obesity.
Figure 11E:
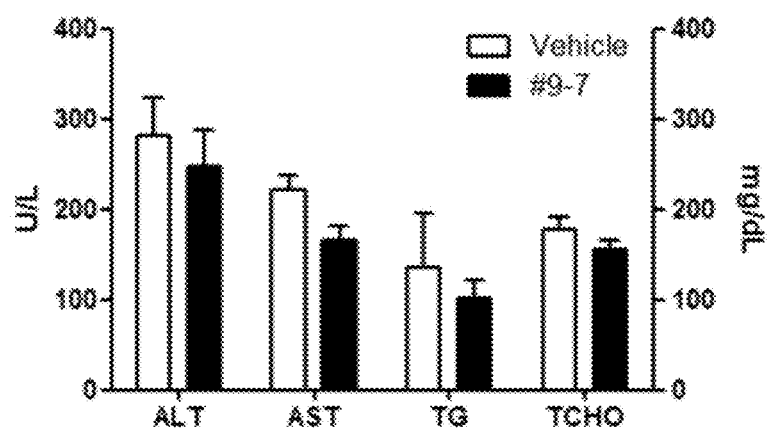

We also chemically modified MSL to generate derivatives of MSL with better efficacy and druggability. Among several derivatives, we tested the effect of a chemical (MSL-7, compound of formula 2) showing definite autophagy-enhancing activity (FIG. 10A) but without cellular toxicity or mTOR inhibition (FIG. 10B). MSL-7 also induced nuclear translocation of TFEB, similar to MSL (FIG. 10C). When administered to ob/ob mice, MSL-7 significantly improved non-fasting blood glucose level without significant effect on body weight (FIGS. 11A and 11B). IPGTT and ITT also demonstrated significantly improved glucose tolerance and insulin sensitivity, respectively (FIGS. 11C and 11D).

Figure 14:
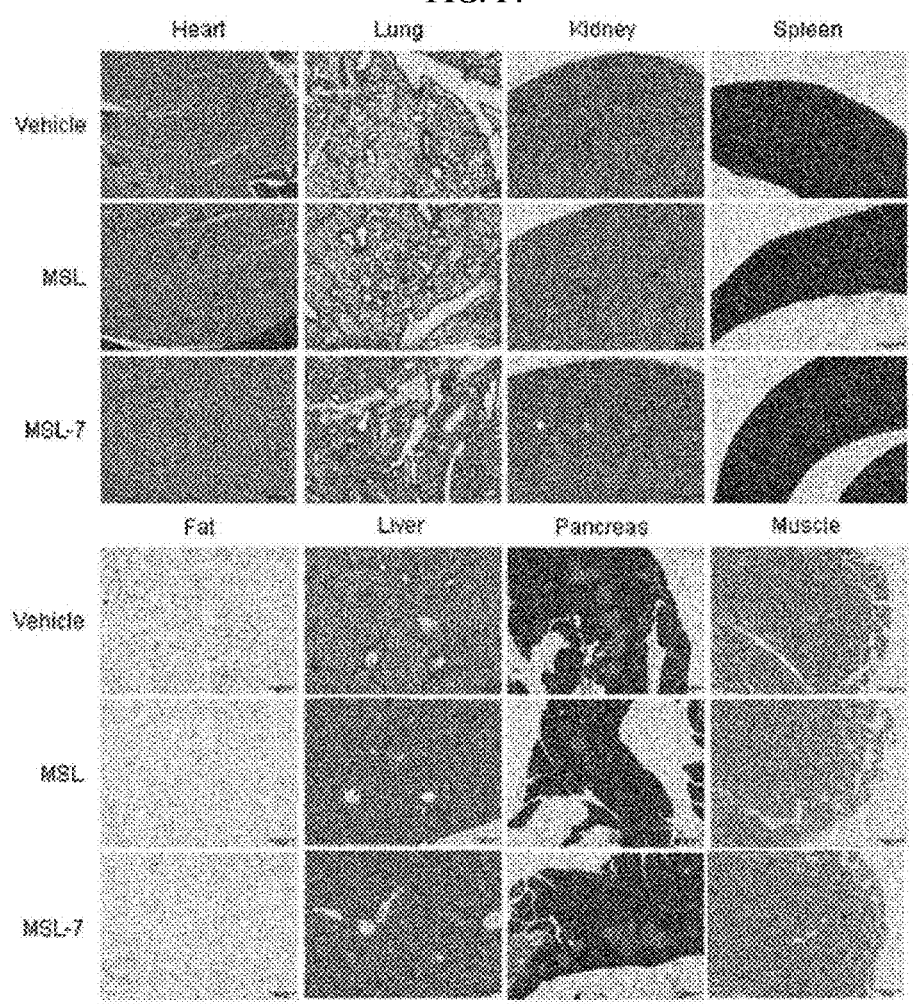
FIG. 14 indicates that the administration of MSL or MSL-7 of the present compound in vivo has no harmful effect or not toxic as evidenced by major organ sample biopsy. Organs were harvested from ob/ob mice administered with MSL or MSL-7 for 8 weeks and stained with H&E for histological analysis. It was found that the fatty liver was improved. Other than that, no significant changes were observed (Scale Bar. 500 μm). This indicates that the present MSL or MSL-7 are not toxic to major organs after its administration in vivo thus indicating the potential as a therapeutic agent.

Finally, we studied whether MSL or MSL-7 has systemic toxicity. CBC was not changed by MSL or MSL-7 (Table 1). Biopsy of the major organs such as the heart, kidney, muscle, spleen, lung and pancreas revealed no significant alteration of tissue histology suggesting no significant toxicity on those organs (FIG. 14).

Figure 12A:
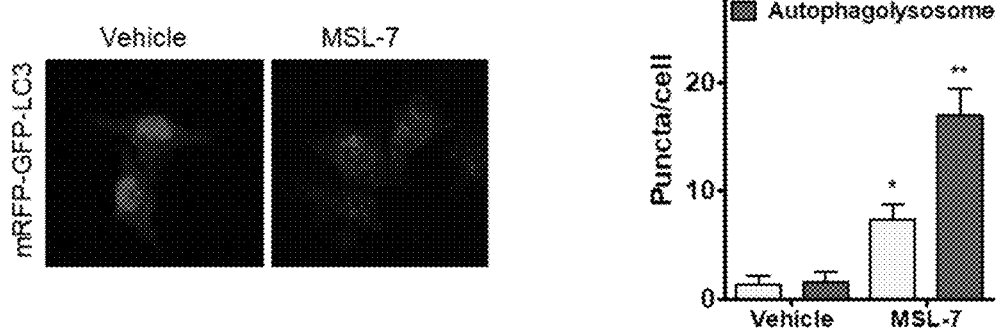
(FIG. 12A) Confocal microscopic result of HeLa cells transfected with tandem mRFP-GFP-LC3 and treated with MSL-7 in which red puncta indicates autophagolysosome.
Figure 12B:
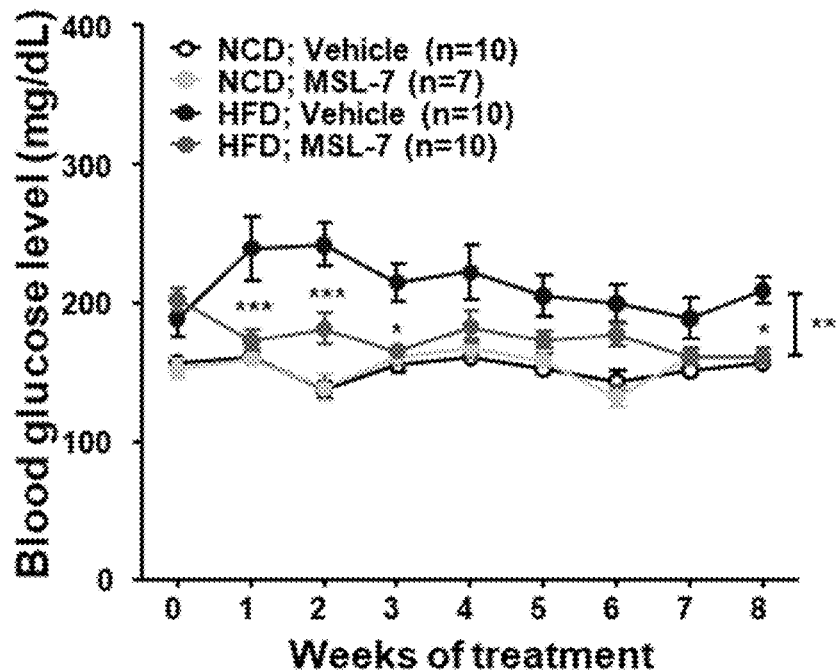
(FIG. 12B, 12C) 8 week old male C57BL/6 mice were fed with HFD or normal chow diet (NCD) for 8 weeks, and then 50 mg/kg MSL-7 was administered three times a week for 8 weeks. Non-fasting glucose level (FIG. 12B) and body weight (FIG. 12C) were monitored.
Figure 12C:
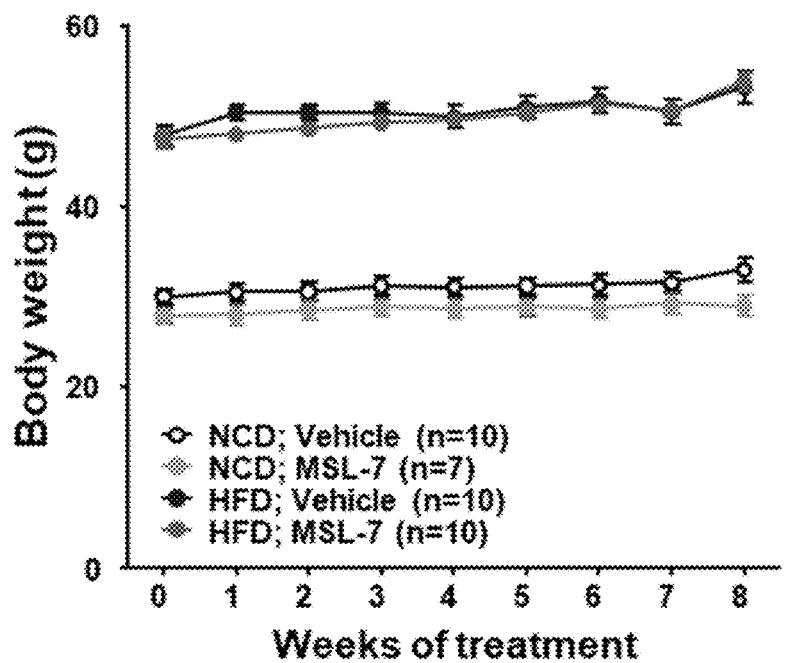
Figure 12D:
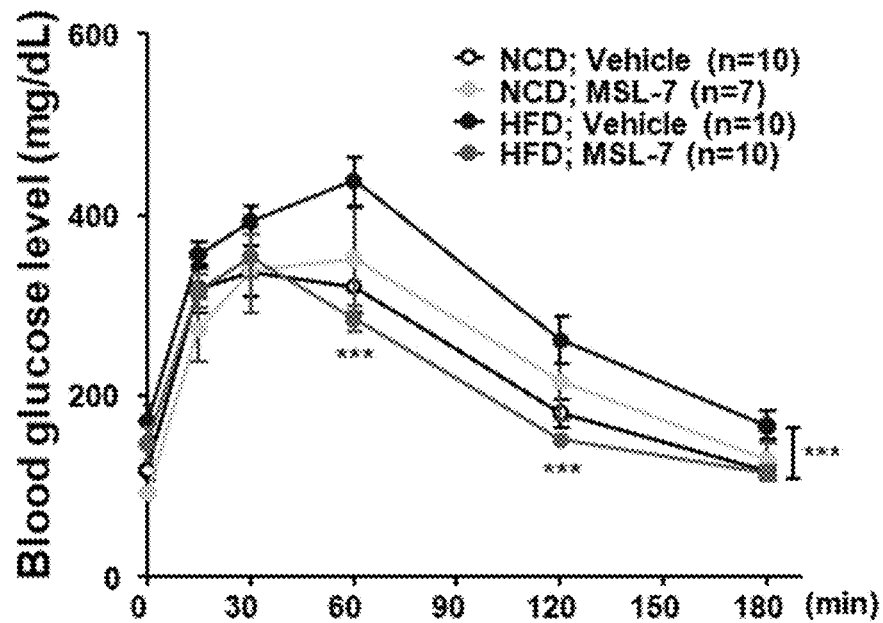
(FIG. 12D) IPGTT.
Figure 12E:
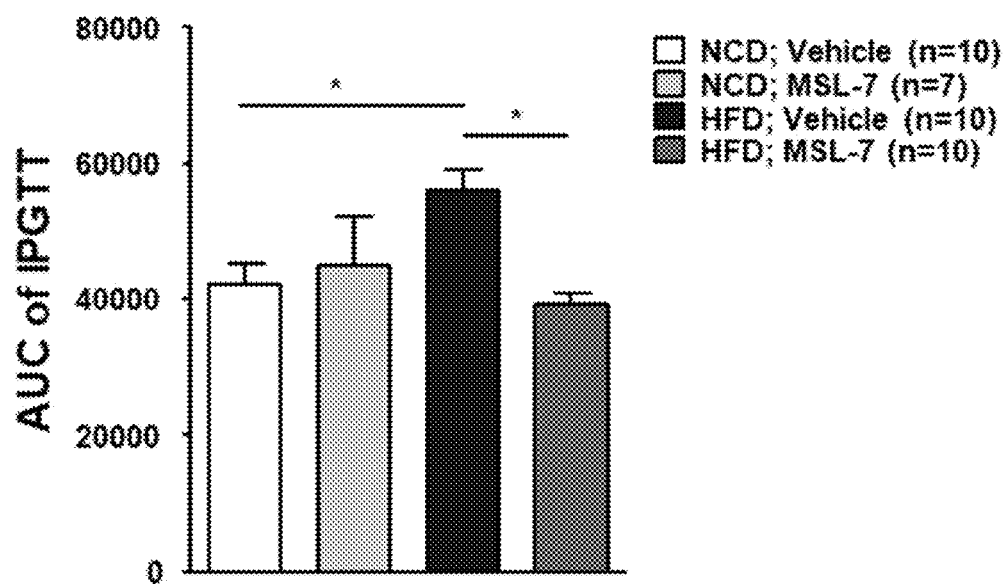
(FIG. 12E) AUC curve of (FIG. 12D).
Figure 12F:
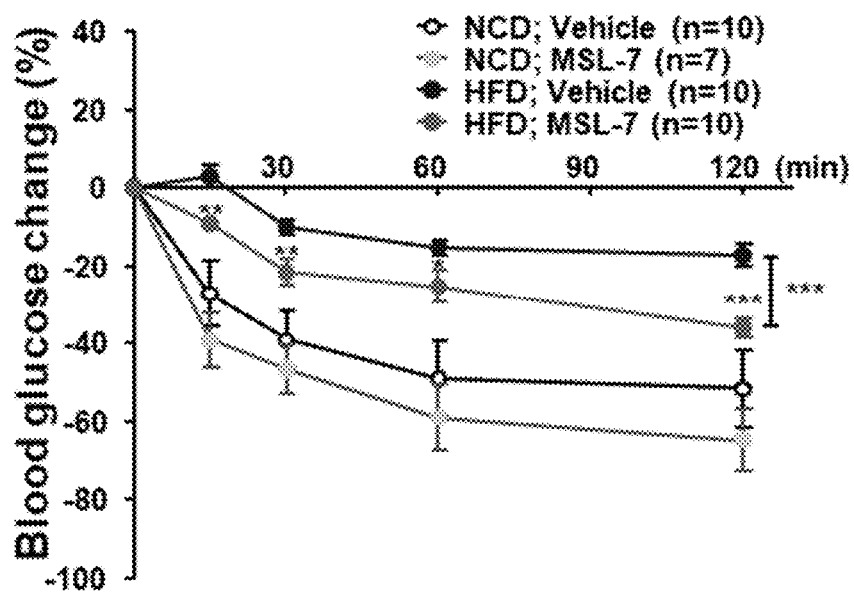
(FIG. 12F) ITT.
Figure 12G:
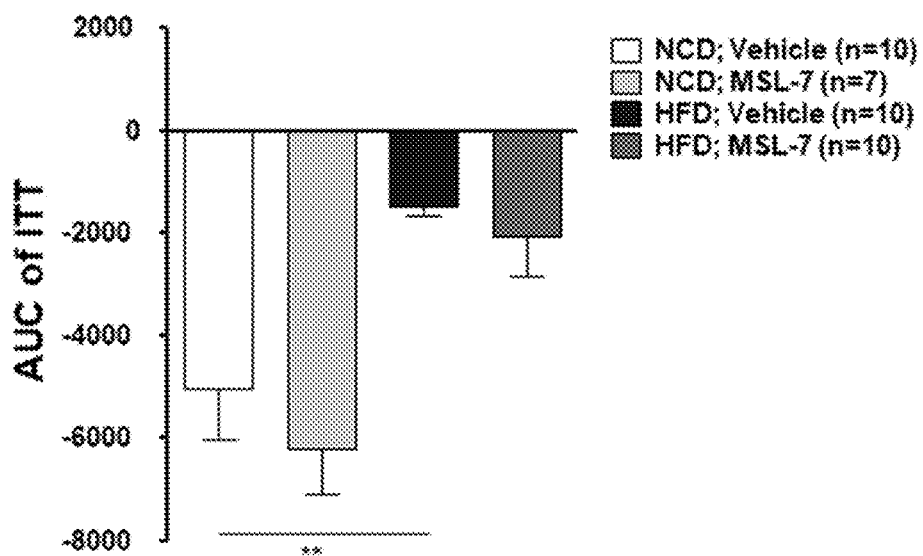
(FIG. 12G) AUC curve of (FIG. 12F). The results indicate that MSL-7, a derivative of MSL, is more effectively improve the metabolic disease due to high fat diet compared to MSL.

Example 7. Improved Metabolic Profile of Obese Mice by Autophagy Enhancer of the Present Invention We next studied whether autophagy enhancement by MSL could improve metabolic profile of obese mice in vivo using obese mouse model due to diet which is more physiologically adept than ob/ob mice. MSL administration for 8 weeks reduced non-fasting blood glucose level and glucose intolerance in mice fed high-fat diet (HFD). however, statistical significance was not achieved for most comparisons except a certain point during IPGTT. One of the reasons metabolic profile of HFD-fed mice was not significantly improved by MSL administration in vivo could be poor microsomal stability of MSL (less than 10% remaining after 30 min incubation with human liver microsome). Thus, we chemically modified MSL to make more efficacious and druggable compounds. Among several derivatives, we selected a chemical (MSL-7) with improved microsomal stability (90.5% remaining after 30 min). We confirmed that MSL-7 induced formation of autophagolysosome, TFEB nuclear translocation and calcineurin activation in a dose-dependent manner (FIG. 12A and FIG. 10C). When administered to ob/ob mice, MSL-7 significantly reduced non-fasting glucose level without changing the body weight (FIG. 12D, 12C). Intraperitoneal glucose tolerance test (IPGTT) and insulin tolerance test (ITT) showed significantly improved glucose tolerance and insulin sensitivity, respectively (FIG. 12D-G), with reduced area under the curves (AUCs). These results indicate that the modified autophagy enhancer of the present disclosure can improve the metabolic profile not only in ob/ob mice but also in HFD fed mice. It was found that MSL-7 does not affect glucose profile of lean or chow-fed mice Example 8. Enhancement Effect on the Function of β-Cell and Metabolic Profile of hIAPP+ Mice by MSL-7

Figure 13A:
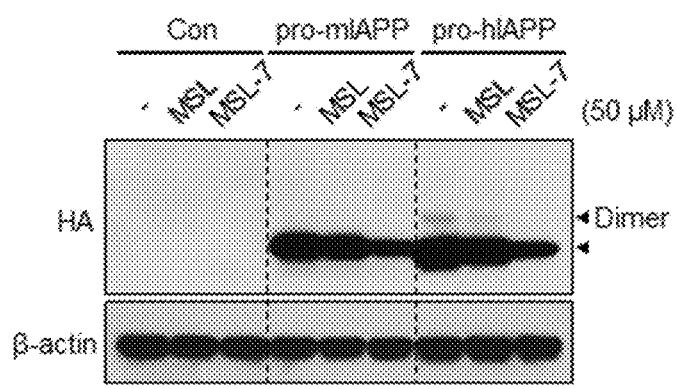
(FIG. 13A) INS-1 cells transfected with non-amyloidogenic prepro-mIAPP-HA or amyloidogenic prepro-hIAPP-HA construct were treated with MSL or MSL-7 followed by western blot analysis using anti-HA antibody.
Figure 13B:
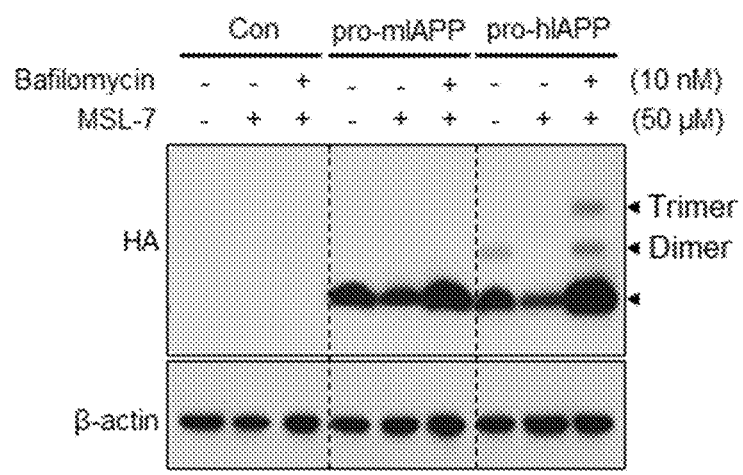
(FIG. 13B) the transfected cells of (FIG. 13A) were treated with MSL-7 in the presence or absence of bafilomycin followed by western blot analysis using anti-HA antibody.
Figure 13C:
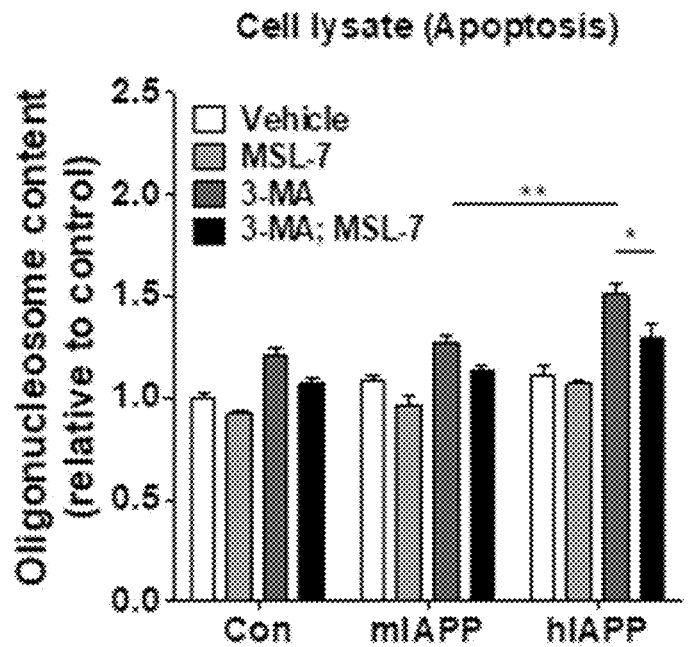
(FIG. 13C) The transfected cells were treated with MSL-7 in the presence or absence of 3-MA, after which the amount of oligonucleosome contained in the cell lysates were measured.
Figure 13D:
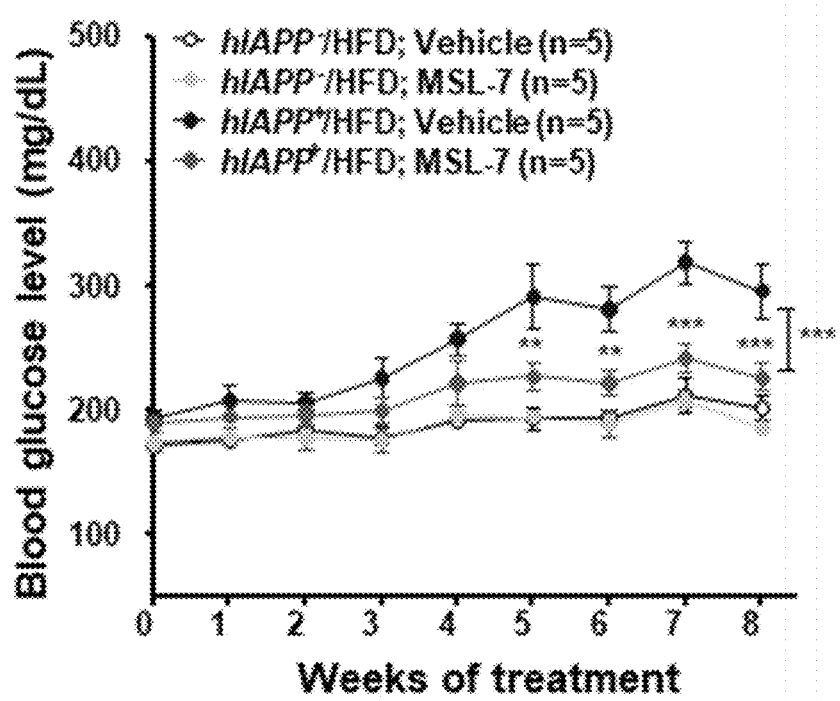
(FIG. 13D) HFD-fed hIAPP+ mice were administered with MSL-7, and non-fasting glucose level was monitored.
Figure 13E:
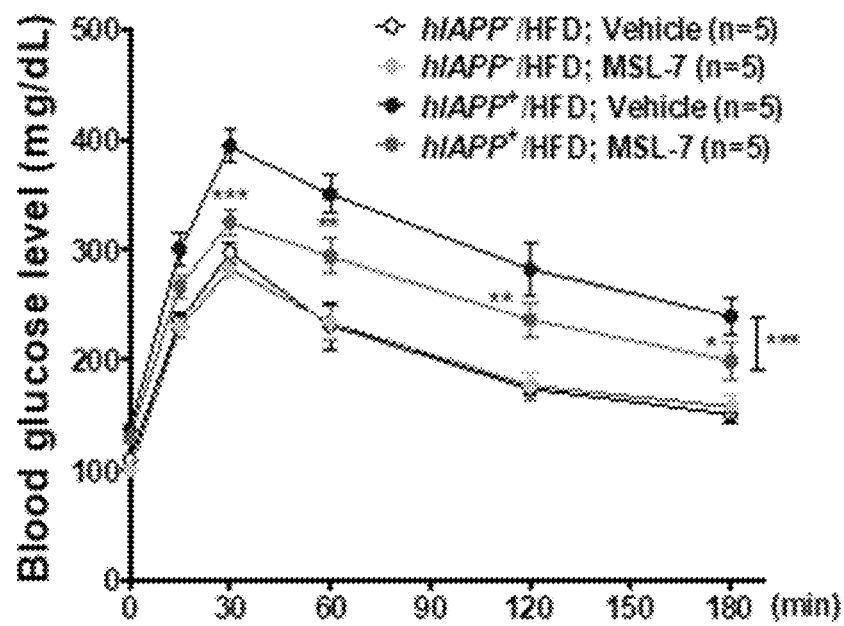
(FIG. 13E) IPGTT.
Figure 13F:
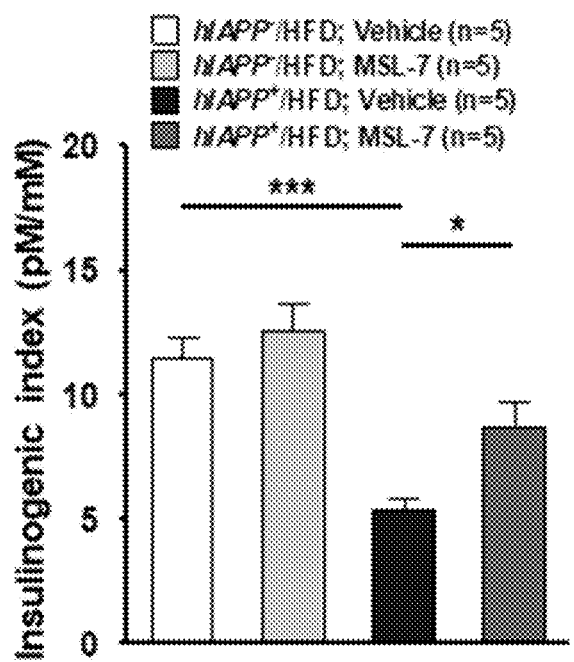
(FIG. 13F) HFD-fed hIAPP+ mice were administered with MSL-7 for 8 weeks and the insulinogenic index was measured.
Figure 13G:
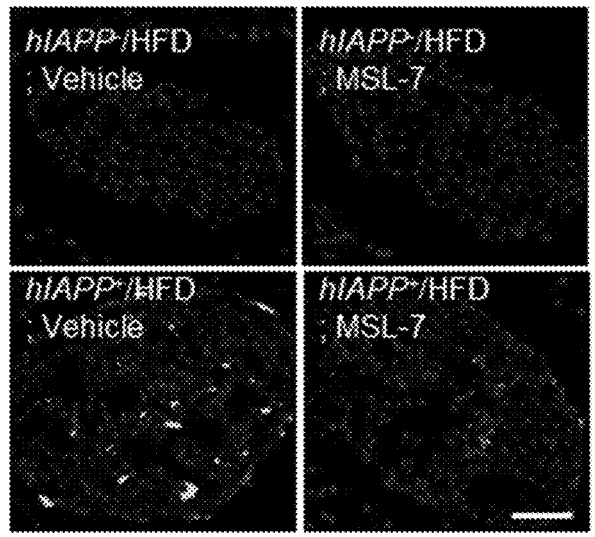
(FIG. 13G) HFD-fed hIAPP+ mice were administered with MSL-7 for 8 weeks and the pancreatic section was obtained. All antibody was used for immunohistochemistry (left). The percentage of A11-duatorehls cells among DAPI+ cells (right).
Figure 13G:
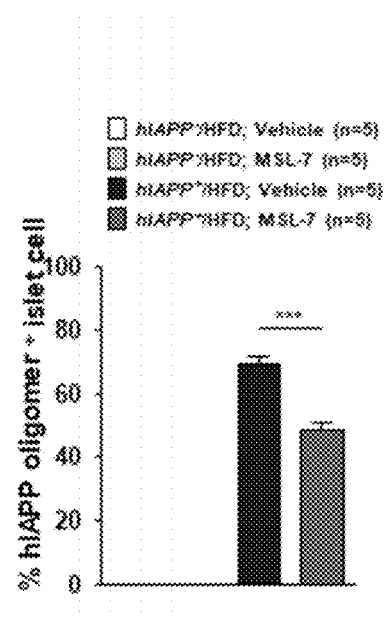
Figure 13H:
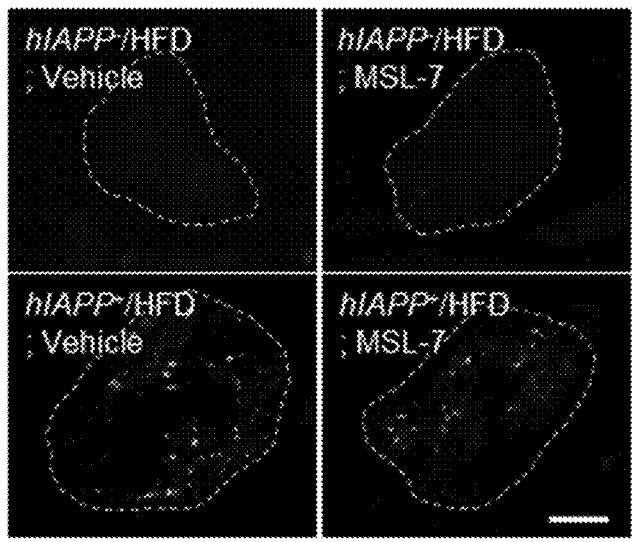
(FIG. 13H) FSB stained pancreatic section of HFD-fed hIAPP+ mice administered with MSL-7 for 8 weeks (left). Average fluorescence intensity/area (right). The results indicate that MSL-7, a derivative of MSL of the present disclosure, can improve the disease by improving the metabolic profile and the function of β-cell of mice having diabetes of human type.
Figure 13H:
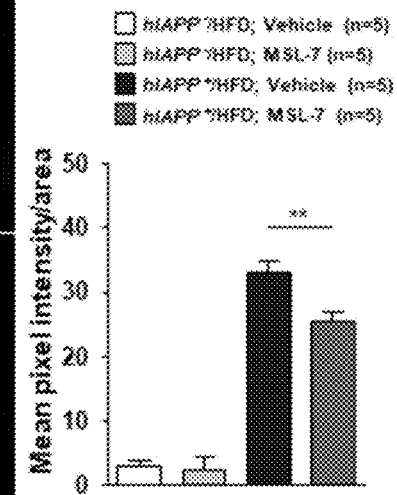

Diabetes of human and murine are different from each other in that >90% of human, pancreatic islet amyloids are accumulated not in murine diabetes. This is due to the difference in the amino acid sequence of the pancreatic islet related polypeptide (IAPP)(Westermark et al. (2011) Islet amyloid polypeptide, islet amyloid, and diabetes mellitus. Physiol Rev. July; 91(3):795-826). In the present invention, the effect of the present autophagy enhancer on the accumulation of toxic human-type IAPP(hIAPP) oligomer which is regulated by autophagy was analyzed. As a result, both MSL and MSL-7, in INS-1 insulinoma cells transfected with amyloidogenic prepro-hIAPP, reduced the accumulation of pro-hIPP dimers, and the effect of MSL-7 was found to become more profoud (FIG. 13A). The decrease of the accumulation of pro-hIAPP by MSL-7, as evidenced by the recovery of pro-hIAPP dimer and the appearance of pro-hIAPP trimer, disappeared by bafillomycin treatment (FIG. 13B). This indicates that MSL-7 decreases the accumulation of pro-hIAPP dimer by enhancing the autophagy activity. When apoptosis due to hIAPP oligomer accumulation was studied (Kim et al., 2014, ibid), MSL-7 treatment significantly reduced the apoptosis of the cells tranfected with prepro-hIAPP in the presence of 3-MA (FIG. 13C), indicating that this is caused by the elimination of hIAPP oligomer by MSL-7. Also MSL-7 administration significantly reduced the non-fasting glucose level of transgenic mice (hIAPP+ mice) expressing hIAPP in pancreatic β-cell, which induces diabetes by HFD (FIG. 13D). Glucose intolerance and insulinogenic index that indicates dysfunction of β-cell function after HFD also was significantly improved by the 8 week treatment of MSL-7 (FIG. 13E, 13F). This proves the effect of the present autophagy enhancer on human type diabetes in vivo. In the present disclosure, immuno-staining was performed using A11 antibody to detect hIAPP oligomers. The accumulation of hIAPP oligomer in hiAPP+ mice that is promoted by HFD was significantly reduced by the 8-week administration of MSL-7. This indicates that MSL-7 improves the clearance of hIAPP oligomer. EE-1-Fluoro-2, 5-bis (3-hydroxycarbonyl-4-hydroxy) styrylbenzene (FSB)-stained pancreatic islet amyloid in HFD-fed hIAPP+ mice was found to be similarly reduced by the 8-week administration of MSL-7 (FIG. 13H). This demonstrates the effect of MSL-7 on the accumulation of amyloid in pancreatic islet.

Finally, in the present disclosure, the toxicity of the present enhancers were tested. The 8-week treatment of MSL or MSL-7 improved the metabolic profile, and reduced the level of liver enzymes (Table 1 below). Other than that the administration does not affect the hemogram or blood chemistry of ob/ob mice. In the major organ biopsy, there were found no side effects. Rather the fatty liver was improved (FIG. 14). This also indicates that MSL or MSL-7 of the present disclosure do not have any significant toxicity and supports their potential druggability.

TABLE 1

|  |  | Normal Range | Vehicle | MSL | MSL-7 |
|---|---|---|---|---|---|
| Leukocytes | WBC | 1.8-10.7 (K/μL) | 6.48 ± 0.78 | 7.64 ± 1.54 | 6.26 ± 0.52 |
|  | NEU | 0.1-2.4 (K/μL) | 1.91 ± 0.24 | 2.34 ± 0.51 | 1.97 ± 0.16 |
|  | LYM | 0.9-9.3 (K/μL) | 3.93 ± 0.47 | 4.73 ± 0.95 | 3.97 ± 0.38 |
|  | MONO | 0.0-0.4 (K/μL) | 0.35 ± 0.08 | 0.35 ± 0.109 | 0.28 ± 0.05 |
|  | EOS | 0.0-0.2 (K/μL) | 0.17 ± 0.08 | 0.165 ± 0.06 | 0.04 ± 0.01 |
|  | BASO | 0.0-0.2 (K/μL) | 0.05 ± 0.02 | 0.05 ± 0.01 | 0.01 ± 0.01 |
| Erythrocytes | RBC | 6.36-9.42 (M/μL) | 9.39 ± 0.53 | 8.82 ± 0.54 | 9.22 ± 0.12 |
|  | HGB | 11.0-15.1 (g/dL) | 13.86 ± 0.52 | 14.30 ± 0.56 | 13.60 ± 0.19 |
|  | HCT | 38.5-59.0 (%) | 50.5 ± 2.4 | 46.9 ± 2.4 | 49.25 ± 0.78 |
| Thrombocytes | PLT | 592-2972(K/μL) | 926 ± 38 | 1081 ± 61 | 1031 ± 55 |

|  | Vehicle | MSL | MSL-7 |
|---|---|---|---|
| AST (U/L) | 222.2 ± 15.30$^a$ | 158.1 ± 16.39$^c$ | 153.8 ± 12.81$^b$ |
| ALT (U/L) | 281.7 ± 42.52$^a$ | 183.7 ± 35.71$^b$ | 146.9 ± 21.59$^b$ |
| TG (mg/dL) | 134.4 ± 60.66$^a$ | 13.9 ± 16.41$^a$ | 78.6 ± 22.50$^b$ |
| TCHO (mg/dL) | 177.2 ± 14.32 | 150 ± 12.22 | 136.9 ± 9.73 |
| ALP (U/L) | 518.3 ± 57.83$^a$ | 267 ± 35.02$^b$ | 278 ± 26.11$^b$ |
| ALB (g/dL) | 1.08 ± 0.83 | 1.1 ± 0.10 | 1.1 ± 1.0 |
| DBIL (mg/dL) | <0.5 | <0.5 | <0.5 |
| GGT (U/L) | <5 | <5 | <5 |
| LDH (U/L) | 1848.3 ± 91.79$^a$ | 1428 ± 148.90$^b$ | 810 ± 112.40$^c$ |
| CRE (mg/dL) | 1 ± 0 | 0.75 ± 0.14 | 1 ± 0 |
| CPK (U/L) | 336.7 ± 48.7 | 323.8 ± 29.68 | 241.3 ± 18.19 |
| CA (mg/dL) | 11.17 ± 0.44 | 11.13 ± 0.24 | 10.75 ± 0.32 |
| BUN (U/L) | 19.17 ± 0.67 | 21.13 ± 1.38 | 20 ± 0.89 |

Table 1 indicates the hemogram and blood chemistry analyzed after administration of the present autophagy enhancer for 8 week in vivo. It was found that liver enzymes and TG blood level is reduced and the metabolic profile is improved. Other than that, there are no adverse changes were found. The serum TG level and LDH level was significantly lower in mice administered with MSL-7 compared to MSL (WBC, while blood cell; NEU, neutrophil; LYM, lymphocyte; MONO, monocyte; EOS, eosinophil; BASO, basophil; RBC, red blood cell; HGB, hemoglobin; HCT, hematocrit; PLT, platelet; TG, triglyceride; TCHO, total cholesterol; ALP, alkaline phosphatase; ALB, albumin; DBIL, direct bilirubin; GGT, g-glutamyltransferase; LDH, lactate dehydrogenase; CRE, creatinine; CPK, creatine phosphokinase; CA, Ca2+; BUN, bloodureanitrogen).

In summary, two main factors for causing type 2 diabetes are insulin resistance and dysfunction of beta cells. However, the molecular mechanism underlying the above factors has not been identified at the molecular and cellular level. Excess accumulation of lipids, low grade inflammation due to chemokine and cytokines, NF-kB and JNK activation are the important molecular mechanism (Vandanmagsar, 2011, ibid). The dysfunction of ER and mitochondria at the level of organelles and stress are also known as critical factors for the development of diabetes (Ozcan et al. (2004) Endoplasmic reticulum stress links obesity, insulin action, and type 2 Diabetes. Science 306, 457-461), and this may affect the above described mechanism at the upper or lower level. The autophagic activity is reduced significantly in the excess lipid condition and during the senescence. Thus the depletion of autophagy may lead to the dysfunction of ER and mitochondria. Also the depletion of autophagy may underlie the basis for age-related metabolic syndrome and diabetes. In contrast, inducing the autophagic activity may provide a new approach to treat metabolic disease or diabetes. This is different from the previous notion that autophagy is a basal defect that constitutes a diabetic pathogenesis rather than an abnormal molecular or cellular process due to underlying defects. Previously, the association of autophagy with the development of disease has been mainly studied in cancer, neurodegenerative diseases, and infectious diseases, and its role in metabolic diseases has not been reported. The present disclosure indicates that it is possible to treat the metabolic disease by regulating the autophagy.

While one or more exemplary embodiments have been described with reference to the figures, it will be understood by those of ordinary skill in the art that various changes in form and details may be made therein without departing from the spirit and scope of the inventive concept as defined by the following claims.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited.

What is claimed is:

1. A compound of Formula 2:

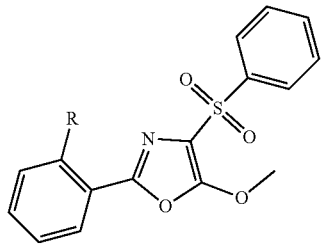

[Formula 2]

wherein R is F, Cl or Br.

2. A pharmaceutical composition comprising the compound according to claim 1 or a pharmaceutical salt thereof.

3. The pharmaceutical composition of claim 2, wherein the composition is for treating or preventing a metabolic disorder comprising one or more symptoms of an insulin resistance, Type 2 diabetes, hyperlipidemia, fatty liver, obesity and inflammation.

4. A method of treating a metabolic disorder in a subject in need thereof, comprising administering to the subject an effective amount of the compound of claim 1.

5. A method of treating a metabolic disorder in a subject in need thereof, comprising administering to the subject an effective amount of the composition of claim 2.

6. The method of claim 4, wherein the metabolic disease comprises one or more symptoms of an insulin resistance, Type 2 diabetes, hyperlipidemia, fatty liver, obesity or inflammation.

7. The method of claim 5, wherein the metabolic disease comprises one or more symptoms of an insulin resistance, Type 2 diabetes, hyperlipidemia, fatty liver, obesity or inflammation.

* * * * *